US007339035B2

(12) United States Patent
Yanagisawa et al.

(10) Patent No.: US 7,339,035 B2
(45) Date of Patent: Mar. 4, 2008

(54) ANTIBODY RECOGNIZING GM1 GANGLIOSIDE-BOUND AMYLOID β-PROTEIN AND DNA ENCODING THE ANTIBODY

(75) Inventors: Katsuhiko Yanagisawa, 36-3, Gengo, Morioka-cho, Obu-shi, Aichi 474-0031 (JP); Masao Shibata, Ina (JP)

(73) Assignees: Medical & Biological Laboratories Co., Ltd., Nagoya-shi (JP); Japan as Represented by the Director of Chubu National Hospital, Obu-shi (JP); Katsuhiko Yanagisawa, Obu-shi (JP)

( * ) Notice: Subject to any disclaimer, the term of this patent is extended or adjusted under 35 U.S.C. 154(b) by 260 days.

(21) Appl. No.: 10/768,193

(22) Filed: Feb. 2, 2004

(65) Prior Publication Data

US 2004/0181042 A1 Sep. 16, 2004

Related U.S. Application Data

(63) Continuation of application No. PCT/JP02/07874, filed on Aug. 1, 2002.

(30) Foreign Application Priority Data

Aug. 3, 2001 (JP) ............................. 2001-235700

(51) Int. Cl.
*C07K 16/28* (2006.01)
*C07K 16/00* (2006.01)
(52) U.S. Cl. ............................. 530/388.25; 530/387.3; 530/387.1
(58) Field of Classification Search .................... None
See application file for complete search history.

(56) References Cited

U.S. PATENT DOCUMENTS 5,530,101 A * 6/1996 Queen et al. ............. 530/387.3

FOREIGN PATENT DOCUMENTS

EP 620 276 A1 * 12/1990
WO WO 90/07861 7/1990

OTHER PUBLICATIONS

Paul WE. Fundamental Immunology, 1993, Raven Press, New York, pp. 292-295.*
Radikoff S et al. Single amino acid substitution altering antigen-binding specificity. Proc Natl Acad Sci USA, 1982; 79: 1979-1983.*
Webber KO et al. Preparation and characterization of a disulfide-stabilized Fv fragment of the anti-Tac antibody: comparison with its single-chain analog. Mol Immunol, 1995; 32(4): 249-258.*
Yanagisawa et al., "GM1 Ganglioside-Bound Amyloid β-Protein (Aβ): A Possible Form of Preamyloid in Alzheimer's Disease", Nature Medicine, vol. 1, No. 10, pp. 1062-1066, 1995.
Yanagisawa et al., "GM1 Ganglioside-Bound Amyloid β-Protein in Alzheimer's Disease Brain", Neurobiology of Aging, vol. 19, No. 1S, pp. S65-S67, 1998.
Yanagisawa et al., "Amyloid β-Protein (Aβ) Associated with Lipid Molecules: Immunoreactivity Distinct From that of Soluble Aβ", FEBS Letters 420 (1997) 43-46.
McLaurin et al., "Membrane Disruption by Alzheimer β-Amyloid Peptides Mediated . . . ", Journal of Biological Chemistry, vol. 271, No. 43, pp. 26482-26489, 1996.
Choo-Smith et al., "The Interaction between Alzheimer Amyloid β(1-40) Peptide and Ganglioside $G_{M1}$-Containing Membranes", FEBS Letters 402 (1997) 95-98.
Choo-Smith et al., "Acceleration of Amyloid Fibril Formation by Specific Binding of Aβ-(1-40) Peptide . . . ", Journal of Biological Chemistry, vol. 272, No. 37, pp. 22987-22990, 1997.
Matsuzaki et al., "Interactions of Amyloid β-Peptide (1-40) with Ganglioside-Containing Membranes", Biochemistry 1999, 38, 4137-4142.
Koppaka et al., "Accelerated Accumulation of Amyloid β Proteins on Oxidatively Damaged Lipid Membranes", Biochemistry 2000, 39, 10011-10016.
Kakio et al., "Cholesterol-dependent Formation of GM1 Ganglioside-Bound Amyloid β-Protein, an Endogenous . . . ", Journal of Biological Chemistry, vol. 276, No. 27, pp. 24985-24990, 2001.
Igbavboa et al., "Increasing Age Alters Transbilayer Fluidity and Cholesterol Asymmetry in Synaptic . . . ", J. Neurochem. 66, 1717-1725 (1996).
Igbavboa et al., "Transbilayer Distribution of Cholesterol Is Modified in Brain Synaptic Plasma Membranes . . . ", J. Neurochem. 69, 1661-1667 (1997).
R.G. Parton, "Ultrastructural Localization of Gangliosides; $GM_1$ Is Concentrated in Caveolae", Journal of Histochemistry and Cytochemistry, vol. 42, No. 2, pp. 155-166, 1994.
Simons et al., "Functional Rafts in Cell Membranes", Nature vol. 387, pp. 569-572, 1997.
Lee et al., "A Detergent-Insoluble Membrane Compartment Contains Aβ in Vivo", Nature Medicine, vol. 4, No. 6, pp. 730-734, 1998.
Morishima-Kawashima et al., "The Presence of Amyloid β-Protein in the Detergent-Insoluble Membrane . . . ", Biochemistry, vol. 37, No. 44, pp. 15247-15253, 1998.
Sawamura et al., "Mutant Presenilin 2 Transgenic Mice . . . ", Journal of Biological Chemistry, vol. 275, No. 36, pp. 27901-27908, 2000.

(Continued)

*Primary Examiner*—Elizabeth C. Kemmerer
*Assistant Examiner*—Kimberly A. Ballard
(74) *Attorney, Agent, or Firm*—Edwards Angell Palmer & Dodge LLP

(57) ABSTRACT

It is intended to provide an antibody efficacious in diagnosing, preventing or treating Alzheimer's disease, DNA encoding the antibody, a method of screening a drug and drugs. The amino acid sequence and the gene sequence of the variable region of an antibody, which specifically recognizes a GM1 ganglioside-bound amyloid β-protein occurring in the early stage of β-amyloid fibril formation, are determined. Based on the data of the amino acid sequence and the gene sequence thus obtained, an antibody is designed.

7 Claims, 7 Drawing Sheets

OTHER PUBLICATIONS

Kim, et al., "Production and Characterization of Monoclonal Antibodies Reactive to Synthetic Cerebrovascular . . . ", Neuroscience Research Communications vol. 2, No. 3, pp. 121-130, 1988.

Jones et al., "Replacing the Complementarity-Determining Regions in a Human Antibody with Those From a Mouse", Nature vol. 321, No. 6069, pp. 522-525, 1986.

Yanagisawa et al., Internal Medicine, vol. 77, No. 5, pp. 797-803, 1996 (relates to the background of the invention).

Yanagisawa et al., Journal of Clinical and Experimental Medicine, Igaku No Ayumi, vol. 189, No. 1, pp. 3-8, 1999 (relates to the background of the invention).

Hayashi et al; "A Seed for Alzheimer Amyloid in the Brain"; The Journal of Neuroscience, May 19, 2004—24(20): pp. 4894-4902.

Supplementary European Search Report dated Nov. 18, 2004.

European Patent Office Action in counterpart application EP 02 755 765.1, dated Jul. 22, 2005.

* cited by examiner

Fig. 1

Filename        : Aβ antibody heavy chain variable region
Sequence Size   : 408
Sequence Position: 1 - 408 signal sequence
```
         10        20        30        40        50        60
ATGGGATGGATCTGGATCTTTCTCTTCCTCCTGTCAGGAACTGCAGGTGTCCACTCTGAG
 M  G  W  I  W  I  F  L  F  L  L  S  G  T  A  G  V  H  S  E 70        80        90       100       110       120
GTCCAGCTGCAGCAGTCTGGACCTGAGCTAGTGAAGACTGGGGCTTCAGTGAAGATATCC
 V  Q  L  Q  Q  S  G  P  E  L  V  K  T  G  A  S  V  K  I  S
```

CDR1
```
        130       140       150       160       170       180
TGCAAGGCTTCTGGTTACTCATTCACTGGTTACTACATGCACTGGGTCAAGCAGAGCCAT
 C  K  A  S  G  Y  S  F  T  G  Y  Y  M  H  W  V  K  Q  S  H
```

CDR2
```
        190       200       210       220       230       240
GGAAAGAGCCTTGAGTGGATTGGATATATTAGTTGTTACAATGGTGCTACTAGCTACAAC
 G  K  S  L  E  W  I  G  Y  I  S  C  Y  N  G  A  T  S  Y  N 250       260       270       280       290       300
CAGAAGTTCAAGGGCAAGGCCACATTTACTGTAGACACATCCTCCAGCACAGCCTACATG
 Q  K  F  K  G  K  A  T  F  T  V  D  T  S  S  S  T  A  Y  M
```

CDR3
```
        310       320       330       340       350       360
CAGTTCAACAGCCTGACATCTGAAGACTCTGCGGTCTATTACTGTGCAAGAGGGGCTAAC
 Q  F  N  S  L  T  S  E  D  S  A  V  Y  Y  C  A  R  G  A  N 370       380       390       400
TGGGTCTTTGACTACTGGGGCCAAGGCACCACTCTCACAGTCTCCTCA
 W  V  F  D  Y  W  G  Q  G  T  T  L  T  V  S  S
```

Fig. 2

```
Filename       : Aβ antibody light chain variable region
Sequence Size  : 387
Sequence Position: 1 - 387
``` signal sequence
―――――――――――――――――――――――――――――――――――――――――――――――――――――
         10        20        30        40        50        60
ATGGCCTGGACTTCACTTATACTCTCTCTCCTGGCTCTCTGCTCAGGAGCCAGTTCCCAG
 M  A  W  T  S  L  I  L  S  L  L  A  L  C  S  G  A  S  S  Q 70        80        90       100       110       120
GCTGTTGTGACTCAGGAATCTGCACTCACCACATCACCTGGTGGAACAGTCATACTCACT
 A  V  V  T  Q  E  S  A  L  T  T  S  P  G  G  T  V  I  L  T
                                CDR1
                ┌─────────────────────────────────────┐
        130       140       150       160      │ 170       180
TGT│CGCTCAAGTACTGGGGCTGTTACAACTAGTAACTATGCCAAC│TGGGTCCAAGAAAAA
 C │ R  S  S  T  G  A  V  T  T  S  N  Y  A  N │ W  V  Q  E  K
                                         CDR2
                                    ┌─────────────────────┐
        190       200       210    │  220       230       │240
CCAGATCATTTATTCACTGGTCTAATAGGT│GGTACCAGCAACCGAGCTCCA│GGTGTTCCT
 P  D  H  L  F  T  G  L  I  G │ G  T  S  N  R  A  P │ G  V  P 250       260       270       280       290       300
GTCAGATTCTCAGGCTCCCTGATTGGAGACAAGGCTGCCCTCACCATCACAGGGGCACAG
 V  R  F  S  G  S  L  I  G  D  K  A  A  L  T  I  T  G  A  Q
                                    CDR3
                            ┌─────────────────────────────┐
        310       320       │330       340       350      │360
ACTGAGGATGATGCAATGTATTTCTGT│GCTCTATGGTACAGCACCCATTATGTT│TTCGGC
 T  E  D  D  A  M  Y  F  C │ A  L  W  Y  S  T  H  Y  V │ F  G 370       380
GGTGGAACCAAGGTCACTGTCCTAGGT
 G  G  T  K  V  T  V  L  G Fig. 3
(A)
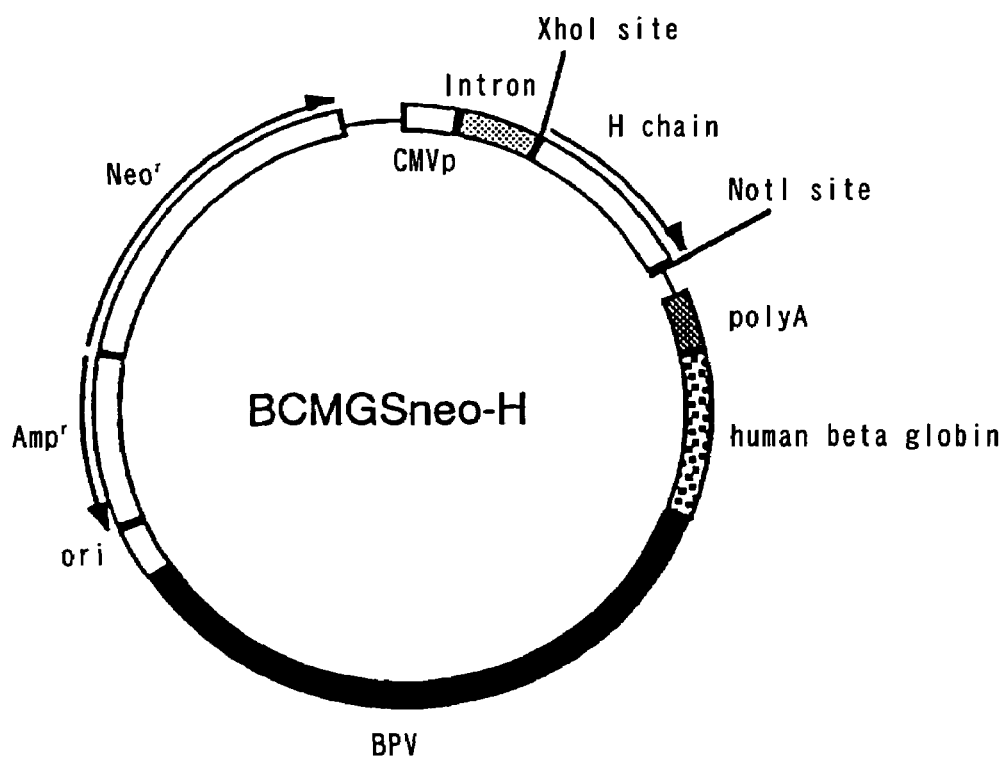
(B)
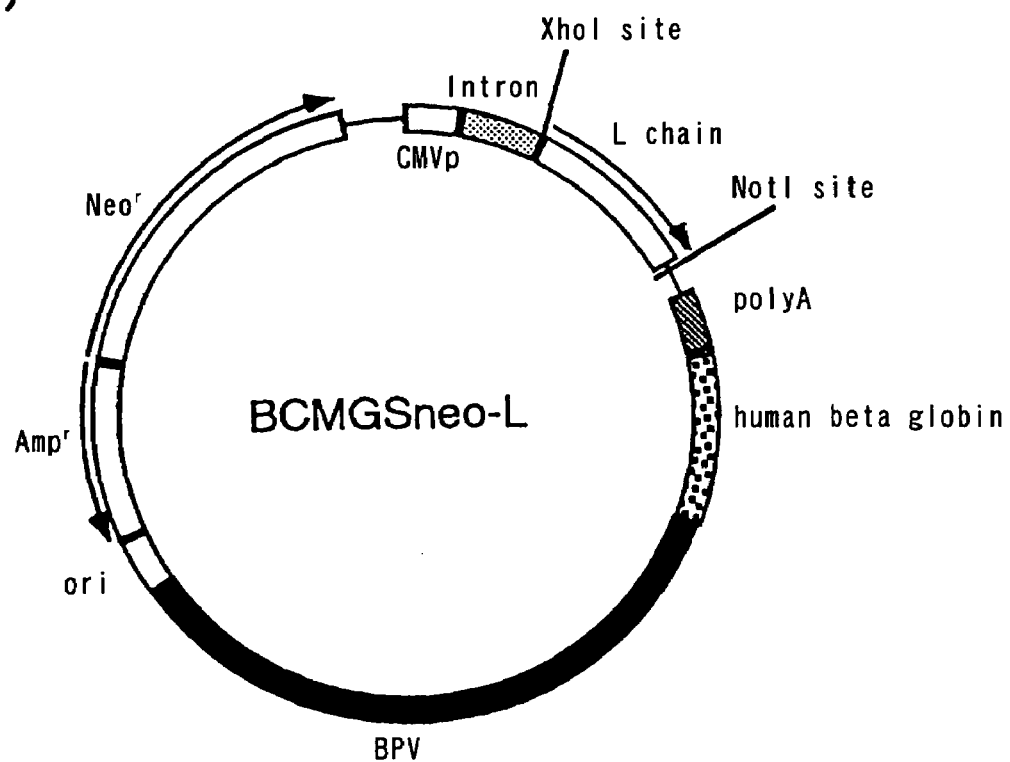

Fig. 4
A
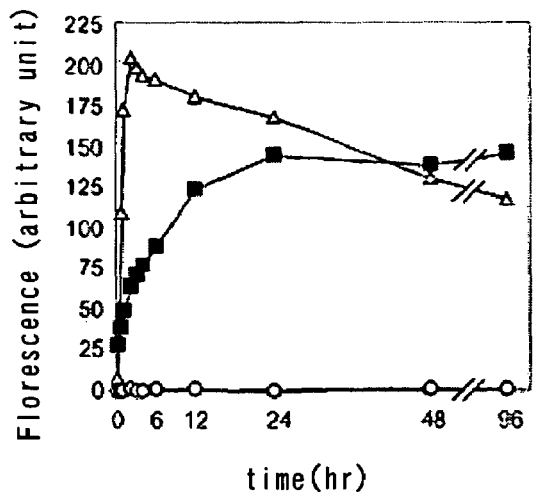
B
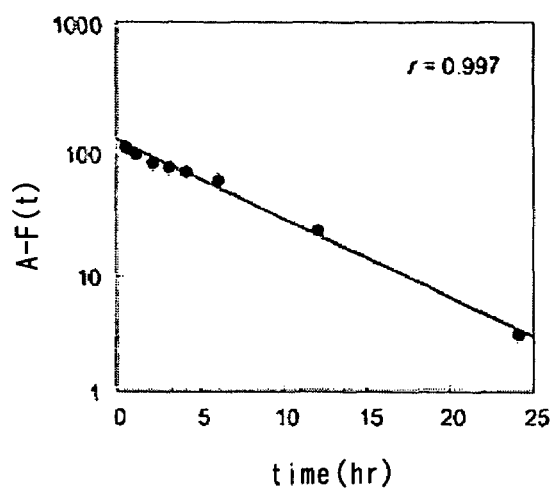
C
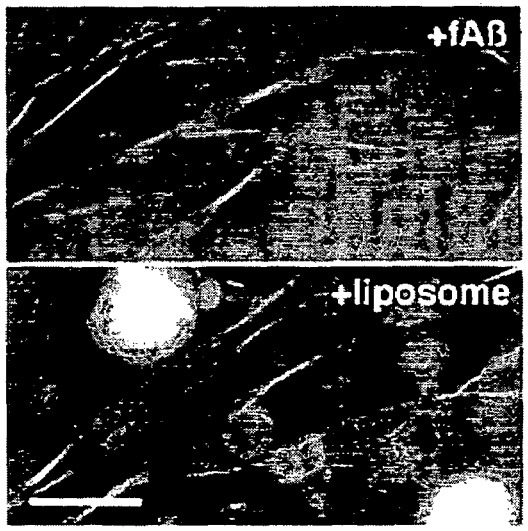

Fig. 5
A
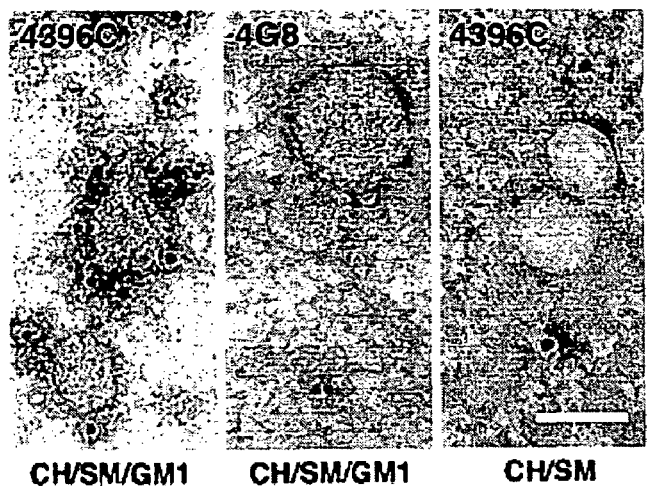
CH/SM/GM1  CH/SM/GM1  CH/SM
B
Aβ — 4396C 4G8    GM1 — 4396C CTX
C
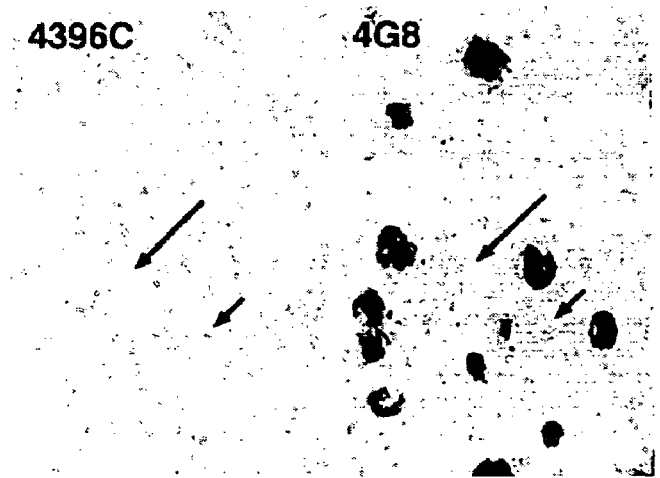

Fig. 6
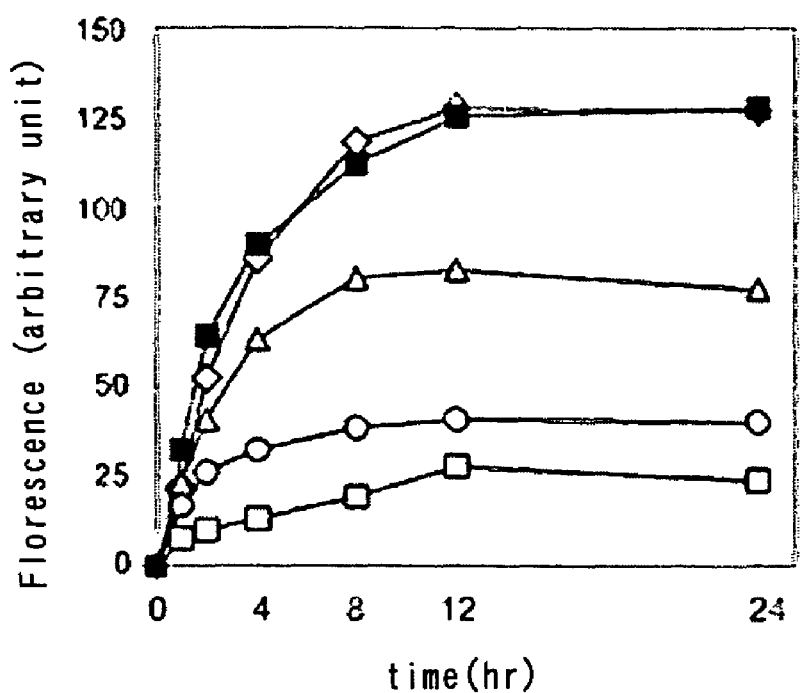
A
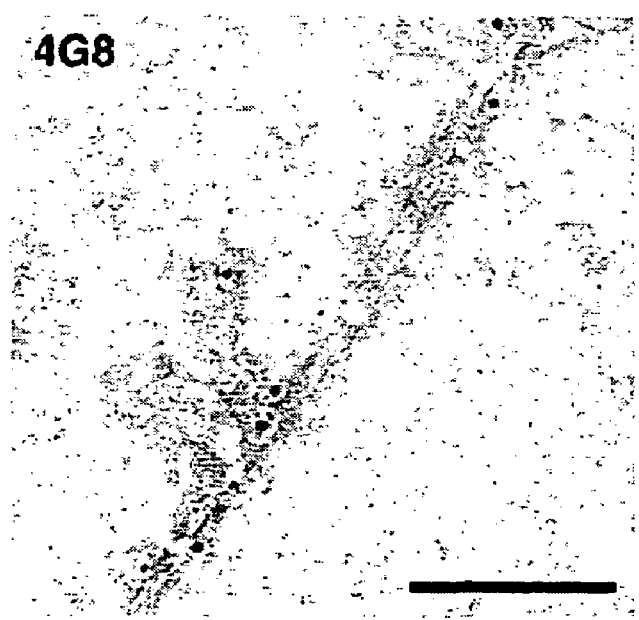
B

SEQUENCE LISTING

```
<160> NUMBER OF SEQ ID NOS: 16

<210> SEQ ID NO 1
<211> LENGTH: 5
<212> TYPE: PRT
<213> ORGANISM: Mus musculus

<400> SEQUENCE: 1

Gly Tyr Tyr Met His
 1               5

<210> SEQ ID NO 2
<211> LENGTH: 17
<212> TYPE: PRT
<213> ORGANISM: Mus musculus

<400> SEQUENCE: 2

Tyr Ile Ser Cys Tyr Asn Gly Ala Thr Ser Tyr Asn Gln Lys Phe Lys
 1               5                  10                  15

Gly

<210> SEQ ID NO 3
<211> LENGTH: 8
<212> TYPE: PRT
<213> ORGANISM: Mus musculus

<400> SEQUENCE: 3

Gly Ala Asn Trp Val Phe Asp Tyr
 1               5
```

<210> SEQ ID NO 4
<211> LENGTH: 14
<212> TYPE: PRT
<213> ORGANISM: Mus musculus

<400> SEQUENCE: 4

Arg Ser Ser Thr Gly Ala Val Thr Thr Ser Asn Tyr Ala Asn
 1               5                  10

<210> SEQ ID NO 5
<211> LENGTH: 7
<212> TYPE: PRT
<213> ORGANISM: Mus musculus

<400> SEQUENCE: 5

Gly Thr Ser Asn Arg Ala Pro
 1               5

<210> SEQ ID NO 6
<211> LENGTH: 9
<212> TYPE: PRT
<213> ORGANISM: Mus musculus

<400> SEQUENCE: 6

Ala Leu Trp Tyr Ser Thr His Tyr Val
 1               5

<210> SEQ ID NO 7
<211> LENGTH: 136
<212> TYPE: PRT
<213> ORGANISM: Mus musculus

<400> SEQUENCE: 7

Met Gly Trp Ile Trp Ile Phe Leu Phe Leu Leu Ser Gly Thr Ala Gly
 1               5                  10                  15

Val His Ser Glu Val Gln Leu Gln Gln Ser Gly Pro Glu Leu Val Lys
                20                  25                  30

Thr Gly Ala Ser Val Lys Ile Ser Cys Lys Ala Ser Gly Tyr Ser Phe
            35                  40                  45

Thr Gly Tyr Tyr Met His Trp Val Lys Gln Ser His Gly Lys Ser Leu
        50                  55                  60

Glu Trp Ile Gly Tyr Ile Ser Cys Tyr Asn Gly Ala Thr Ser Tyr Asn
65                  70                  75                  80

Gln Lys Phe Lys Gly Lys Ala Thr Phe Thr Val Asp Thr Ser Ser Ser
                85                  90                  95

Thr Ala Tyr Met Gln Phe Asn Ser Leu Thr Ser Glu Asp Ser Ala Val
            100                 105                 110

Tyr Tyr Cys Ala Arg Gly Ala Asn Trp Val Phe Asp Tyr Trp Gly Gln
        115                 120                 125

Gly Thr Thr Leu Thr Val Ser Ser
    130                 135

<210> SEQ ID NO 8
<211> LENGTH: 129
<212> TYPE: PRT
<213> ORGANISM: Mus musculus

<400> SEQUENCE: 8

Met Ala Trp Thr Ser Leu Ile Leu Ser Leu Leu Ala Leu Cys Ser Gly
 1               5                  10                  15

-continued

Ala Ser Ser Gln Ala Val Val Thr Gln Glu Ser Ala Leu Thr Thr Ser
            20                  25                  30

Pro Gly Gly Thr Val Ile Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Ser Asn Arg Ala Pro Gly Val Pro
65                  70                  75                  80

Val Arg Phe Ser Gly Ser Leu Ile Gly Asp Lys Ala Ala Leu Thr Ile
                85                  90                  95

Thr Gly Ala Gln Thr Glu Asp Asp Ala Met Tyr Phe Cys Ala Leu Trp
            100                 105                 110

Tyr Ser Thr His Tyr Val Phe Gly Gly Gly Thr Lys Val Thr Val Leu
        115                 120                 125

Gly

<210> SEQ ID NO 9
<211> LENGTH: 408
<212> TYPE: DNA
<213> ORGANISM: Mus musculus
<220> FEATURE:
<221> NAME/KEY: sig_peptide
<222> LOCATION: (1)..(57)
<220> FEATURE:
<221> NAME/KEY: V_region
<222> LOCATION: (1)..(408)

<400> SEQUENCE: 9
atgggatgga tctggatctt tctcttcctc ctgtcaggaa ctgcaggtgt ccactctgag    60
gtccagctgc agcagtctgg acctgagcta gtgaagactg ggcttcagt gaagatatcc    120 tgcaaggctt ctggttactc attcactggt tactacatgc actgggtcaa gcagagccat    180
ggaaagagcc ttgagtggat tggatatatt agttgttaca atggtgctac tagctacaac    240
cagaagttca aggcaaggc cacatttact gtagacacat cctccagcac agcctacatg     300
cagttcaaca gcctgacatc tgaagactct gcggtctatt actgtgcaag aggggctaac    360
tgggtctttg actactgggg ccaaggcacc actctcacag tctcctca                 408

<210> SEQ ID NO 10
<211> LENGTH: 387
<212> TYPE: DNA
<213> ORGANISM: Mus musculus
<220> FEATURE:
<221> NAME/KEY: sig_peptide
<222> LOCATION: (1)..(57)
<220> FEATURE:
<221> NAME/KEY: V_region
<222> LOCATION: (1)..(387)

<400> SEQUENCE: 10
atggcctgga cttcacttat actctctctc ctggctctct gctcaggagc cagttcccag    60
gctgttgtga ctcaggaatc tgcactcacc acatcacctg gtggaacagt catactcact    120
tgtcgctcaa gtactggggc tgttacaact agtaactatg ccaactgggt ccaagaaaaa    180
ccagatcatt tattcactgg tctaataggt ggtaccagca accgagctcc aggtgttcct    240
gtcagattct caggctccct gattggagac aaggctgccc tcaccatcac aggggcacag    300
actgaggatg atgcaatgta tttctgtgct ctatggtaca gcacccatta tgttttcggc    360
ggtggaacca aggtcactgt cctaggt                                        387

```
<210> SEQ ID NO 11
<211> LENGTH: 15
<212> TYPE: DNA
<213> ORGANISM: Mus musculus
<220> FEATURE:
<221> NAME/KEY: V_segment
<222> LOCATION: (1)..(15)

<400> SEQUENCE: 11
ggttactaca tgcac                                                    15

<210> SEQ ID NO 12
<211> LENGTH: 51
<212> TYPE: DNA
<213> ORGANISM: Mus musculus
<220> FEATURE:
<221> NAME/KEY: V_segment
<222> LOCATION: (1)..(51)

<400> SEQUENCE: 12
tatattagtt gttacaatgg tgctactagc tacaaccaga agttcaaggg c             51

<210> SEQ ID NO 13
<211> LENGTH: 24
<212> TYPE: DNA
<213> ORGANISM: Mus musculus
<220> FEATURE:
<221> NAME/KEY: V_segment
<222> LOCATION: (1)..(24)

<400> SEQUENCE: 13
ggggctaact gggtctttga ctac                                          24

<210> SEQ ID NO 14
<211> LENGTH: 42
<212> TYPE: DNA
<213> ORGANISM: Mus musculus
<220> FEATURE:
<221> NAME/KEY: V_segment
<222> LOCATION: (1)..(42)

<400> SEQUENCE: 14
cgctcaagta ctggggctgt tacaactagt aactatgcca ac                      42

<210> SEQ ID NO 15
<211> LENGTH: 21
<212> TYPE: DNA
<213> ORGANISM: Mus musculus
<220> FEATURE:
<221> NAME/KEY: V_segment
<222> LOCATION: (1)..(21)

<400> SEQUENCE: 15
ggtaccagca accgagctcc a                                             21

<210> SEQ ID NO 16
<211> LENGTH: 27
<212> TYPE: DNA
<213> ORGANISM: Mus musculus
<220> FEATURE:
<221> NAME/KEY: V_segment
<222> LOCATION: (1)..(27)

<400> SEQUENCE: 16
gctctatggt acagcaccca ttatgtt                                       27
```

ANTIBODY RECOGNIZING GM1 GANGLIOSIDE-BOUND AMYLOID β-PROTEIN AND DNA ENCODING THE ANTIBODY

CROSS REFERENCE TO RELATED APPLICATIONS

This application is a continuation of international application No. PCT/JP02/07874, filed on Aug. 1, 2002, which claims priority to Japanese application No. 2001-235700, filed on Aug. 3, 2001.

FIELD OF THE INVENTION

The present invention relates to an antibody and a gene encoding the antibody. More particularly, the present invention relates to an antibody associated with Alzheimer's disease and a gene encoding the antibody.

BACKGROUND OF THE INVENTION

In Japan, the aging of population is now progressing at the highest speed that has never been experienced, and along with this, the number of patients with dementia is increasing. According to a survey conducted by the National Institute of Population and Social Security Research, the number of patients with dementia is estimated to reach 1.65 million by 2000 and 2.64 million by 2015. Since cares for such patients with dementia become much economic burden, there have been demands for development of an effective treatment method for the disease as soon as possible.

A major disease of senile dementias is Alzheimer's disease (AD). Although the overview of the pathology of this disease is still unknown, studies are rapidly advancing. Features commonly found in patients with Alzheimer's disease are: (1) atrophy of the brain; (2) deposition of plaque-like substances called senile plaques; and (3) neurofibrillary tangle in which fibrillary substances are deposited inside the neurons. When these three features are found, the patient is diagnosed as Alzheimer's disease. However, except for the feature (1) atrophy of the brain, the formation of senile plaques and the neurofibrillary tangle cannot be found by observation from the outside. This makes it difficult to diagnose Alzheimer's disease. Therefore, there are demands for the development of biological markers such as molecular genetic markers and biochemical markers, which have sufficient specificity and sensitivity, for diagnosing Alzheimer's disease.

A clinical symptom of Alzheimer's disease, i.e., dementia, is closely associated with neuronal loss. As to the reason why the neuronal loss occurs, the above-mentioned pathological changes provide important clues. According to the advancement of studies since the latter half of 1990s, it has been clarified that senile plaques are deposition of aggregated peptides called amyloid β-protein (Aβ). On the other hand, it has been clarified that the neurofibrillary tangle occurs because tau protein, which is one of the scaffold proteins of the neuron, is phosphorylated and aggregated inside the neuron.

Alzheimer's disease is known to occur in two forms, that is, familial Alzheimer's disease caused by genetic factors, and sporadic Alzheimer's disease that is free from genetic reasons. Causative genes or risk factors of familial Alzheimer's disease are becoming clarified. One of the causative genes of familial Alzheimer's disease is a gene encoding Amyloid Precursor Protein (APP). It is known that when this gene contains a mutant, Alzheimer's disease is caused without exception. Therefore, it is thought that if the effect and function of this mutant can be found, the clinical mechanism of Alzheimer's disease would be clarified. Since it is expected that familial Alzheimer's disease and sporadic Alzheimer's disease have a common mechanism, it is thought that some of the researches on the clinical mechanism of familial Alzheimer's disease may be applied to the cases of sporadic Alzheimer's disease.

Aβ is cleaved from an APP with β- and γ-secretases. It has been reported that Aβ includes $A\beta_{40}$ and $A\beta_{42}$ depending on the difference in the cleavage points in which $A\beta_{42}$ is more likely to aggregate than $A\beta_{40}$ and that from the pathological observation, $A\beta_{42}$ firstly aggregates and $A\beta_{40}$ sequentially aggregates around $A\beta_{40}$ as a core to form fibrils. Recent studies by the present inventors provide findings that Aβ starts to be deposited in the AD brain via binding to GM1 ganglioside (GM1) (K. Yanagisawa, A. Odaka, N. Suzuki, Y. Ihara, Nat. Med. 1, 1062 (1995); K. Yanagisawa, Y. Ihara, Neurobiol. Aging 19, S65 (1998)). Furthermore, the present inventors reported that a monoclonal antibody (antibody 4396) that specifically recognizes GM1-bound Aβ was successfully prepared (FEBS Letters 420, 43-46 (1997)). Based on the unique molecular characteristics of this GM1-bound Aβ, the present inventors hypothesized that Aβ adopted an altered conformation via binding to GM1 and functioned as a seed of the formation of amyloid fibrils. Subsequently, several investigators performed in vitro studies and their findings support the above-mentioned hypothesis; i.e., Aβ specifically binds to GM1 on the membranes; soluble Aβ starts to aggregate and form amyloid fibrils following the addition of GM1-containing liposomes (J. McLaurin, A. Chakrabartty, J. Biol. Chem. 271, 26482 (1996); P. Choo-Smith, W. K. Surewicz, FEBS Lett. 402, 95(1997); P. Choo-Smith, W. Garzon-Rodriguez, C. G. Globe, W. K. Sutrewicz, J. Biol. Chem. 272, 22987 (1997); K. Matsuzaki, C. Horikiri, Biochemistry 38, 4137 (1999); V. Koppaka, P. H. Axelsen, Biochemistry 39, 10011 (2000)).

On the other hand, in regard to the molecular mechanism in which GM1-bound Aβ is formed, it has been reported that binding of Aβ to GM1 is dependent on the concentration of cholesterol in the membranes to be bound; i.e., a high concentration of cholesterol enhances the binding of Aβ to GM1 via facilitating the formation of GM1 "cluster" in the membranes (A. Kakio, S. Nishimoto, K. Yanagisawa, Y. Kozutumi, K. Matsuzaki, J. Biol. Chem, 276, 24985 (2001)). Furthermore, Aβ may bind to GM1 on synaptic membranes of the aging brain since the cholesterol concentration in the exofacial leaflets of synaptic membranes significantly increases with age and/or with the deficiency in apolipoprotein E (Apo E) (U. Igbavboa, N. A. Avdulov, F. Schroeder, W. G. Wood, J. Neurochem. 66, 1717 (1996); U. Igbavboa, N. A. Avdulov, S. V. Chochina, W. G. Wood, J. Neurochem. 69, 1661 (1997)). While, Aβ may bind to GM1 in GM1-rich and cholesterol-rich membrane domains (referred to as rafts) since the rafts physiologically contain a large amount of Aβ and in the rafts, insoluble Aβ are deposited in a kind of mouse model with familial Alzheimer's disease (R. G. Parton, J. Histochem. Cytochem. 42, 155 (1994); K. Simons, E. Ikonen, Nature 387, 569 (1997); S. J. Lee et al., Nat. Med. 4, 730 (1998); M. Morishima-Kawashima, Y. Ihara, Biochemistry 37, 15274 (1998); N. Sawamura et al., J. Biol. Chem. 275, 27901 (2000)).

SUMMARY OF THE INVENTION

The present inventions were achieved in light of the above background. It is an object of the present inventions to provide an effective means for treating, diagnosing, or preventing Alzheimer's disease. More particularly, it is an object of the present inventions to provide an antibody that is effective in, for example, treating Alzheimer's disease, and DNA encoding the antibody, as well as a method for screening a drug and drugs.

Firstly, the present inventors have identified the class of the antibody (antibody 4396) that recognizes GM1-bound Aβ. As a result, the class of the antibody was IgM and the L chain was a λ chain. Then, the present inventors attempted to determine sequences of DNAs encoding variable regions of an H chain (heavy chain) and an L chain (light chain) and successfully determined the sequences thereof. Identification of DNA sequences of CDRs of the H chain and L chain was also carried out. Subsequently, a DNA encoding the H-chain variable region was synthesized and a DNA encoding a mouse IgG2a constant region were ligated and thereafter incorporated into an expression vector to form an H-chain expression vector. Similarly, a vector into which a DNA encoding the L chain was incorporated (L-chain expression vector) was prepared. These vectors were transfected into a CHO cell to form transformants. Among the resultant transformants, a transformant with high capacity to produce antibodies was selected, and its culture supernatant was collected and purified. Thus, an IgG antibody having a variable region of the antibody 4396 (hereinafter, also referred to as "antibody 4396C") was successfully obtained.

While the immunological characteristics of the antibody 4396C were investigated, an attempt has been made to resolve the molecular mechanism underlying the initiation of the formation of amyloid fibrils by GM1 using the antibody. Firstly, a liposome having a lipid composition mimic to rafts, which contains GM1 ganglioside (hereinafter, also referred to as "GM1"), cholesterol and sphingomyellin, was prepared. When it was investigated, using the above prepared liposomes, whether or not the antibody 4396C recognizes amyloid β-protein (hereinafter, also referred to as "Aβ") bound to GM1 in the liposomes, specific binding was observed. Then, when it was investigated whether or not the formation of amyloid fibrils was inhibited by the antibody 4396C in the presence of the liposomes, the effect of inhibiting the formation of amyloid fibrils sufficiently and in a manner depending on the additive amount was observed. On the other hand, when a similar experiment was carried out by using a well-known different anti-Aβ antibody, the inhibition of the formation of amyloid fibrils was not observed. Furthermore, it was shown that this different anti-Aβ antibody bound to the end of newly formed amyloid fibrils. These results support the above-mentioned seeding hypothesis. That is to say, it was shown that GM1-bound Aβ (hereinafter, also referred to as "GM1-Aβ") functions as seeds in the formation of amyloid fibrils. Furthermore, unlike the well-known anti-Aβ antibody, since the antibody 4396C specifically binds to this seed, it was found that the structure of the variable region in the antibody 4396C (i.e., the structure of the variable region of the antibody 4396), in particular, the structure of CDR is useful for diagnosis, treatment and the like, for Alzheimer's disease. From such findings, it was thought that the preparation of a humanized antibody having the structure of the variable region of the antibody 4396C, in particular, the structure of the CDR would permit an extremely effective diagnosis, treatment and the like for Alzheimer's disease.

The present invention was accomplished based on the above-mentioned findings, a first aspect of the present invention includes the following configuration.

[1] An antibody having an activity of recognizing GM1 ganglioside-bound amyloid β-protein and inhibiting the formation of amyloid fibrils, the antibody comprising a heavy chain variable region; wherein the heavy chain variable region comprises at least one region of the regions described in a), b) and c):

a) a first region consisting of an amino acid sequence of SEQ ID NO: 1, or the amino acid resulted from a partial alteration of SEQ ID NO: 1;

b) a second region consisting of an amino acid sequence of SEQ ID NO: 2 or the amino acid sequence resulted from a partial alteration of SEQ ID NO: 2; and c) a third region consisting of an amino acid sequence of SEQ ID NO: 3 or the amino acid sequence resulted from a partial alteration of SEQ ID NO: 3.

[2] An antibody having an activity of recognizing GM1 ganglioside-bound amyloid β-protein and inhibiting the formation of amyloid fibrils, the antibody comprising a light chain variable region, wherein the light chain variable region comprises at least one region of the regions described in d), e) and f):

d) a fourth region consisting of an amino acid sequence of SEQ ID NO: 4, or the amino acid sequence resulted from a partial alteration of SEQ ID NO: 4;

e) a fifth region consisting of an amino acid sequence of SEQ ID NO: 5, or the amino acid sequence resulted from a partial alteration of SEQ ID NO: 5; and f) a sixth region consisting of an amino acid sequence of SEQ ID NO: 6, or the amino acid sequence resulted from a partial alteration of SEQ ID NO: 6.

[3] An antibody having an activity of recognizing GM1 ganglioside-bound amyloid β-protein and inhibiting the formation of amyloid fibrils, the antibody comprising: a heavy chain variable region; and a light chain variable region, wherein the heavy chain variable region comprises complementarity determining regions (CDRs) described in g), h) and i), and the light chain variable region comprises CDRs described in j), k) and l);

g) CDR 1 consisting of an amino acid sequence of SEQ ID NO. 1, or the amino acid sequence resulted from a partial alteration of SEQ ID NO: 1;

h) CDR 2 consisting of an amino acid sequence of SEQ ID NO. 2, or the amino acid sequence resulted from a partial alteration of SEQ ID NO: 2;

i) CDR 3 consisting of an amino acid sequence of SEQ ID NO. 3, or the amino acid sequence resulted from a partial alteration of SEQ ID NO: 3;

j) CDR 1 consisting of an amino acid sequence of SEQ ID NO. 4, or the amino acid sequence resulted from a partial alteration of SEQ ID NO: 4;

k) CDR 2 consisting of an amino acid sequence of SEQ ID NO. 5, or the amino acid sequence resulted from a partial alteration of SEQ ID NO: 5; and l) CDR 3 consisting of an amino acid sequence of SEQ ID NO. 6, or the amino acid sequence resulted from a partial alteration of SEQ ID NO: 6.

[4] An antibody having an activity of recognizing GM1 ganglioside-bound amyloid β-protein and inhibiting the formation of amyloid fibrils, the antibody comprising a heavy chain variable region, wherein the heavy chain variable region comprises an amino acid sequence of SEQ ID NO: 7, or the amino acid sequence resulted from a partial alteration of SEQ ID NO: 7.

[5] An antibody having an activity of recognizing GM1 ganglioside-bound amyloid β-protein and inhibiting the formation of amyloid fibrils, the antibody comprising a light chain variable region, wherein the light chain variable region comprises an amino acid sequence of SEQ ID NO: 8, or the amino acid sequence resulted from a partial alteration of SEQ ID NO: 8.

[6] An antibody having an activity of recognizing GM1 ganglioside-bound amyloid β-protein and inhibiting the formation of amyloid fibrils, the antibody comprising: a heavy chain variable region; and a light chain variable region, wherein the heavy chain variable region comprises an amino acid sequence of SEQ ID NO: 7, or the amino acid sequence resulted from a partial alteration of SEQ ID NO: 7; and the light chain variable region comprises an amino acid sequence of SEQ ID NO: 8, or the amino acid sequence resulted from a partial alteration of SEQ ID NO: 8.

[7] The antibody described in any of [1] to [6], which is a humanized antibody.

[8] The antibody described in any of [1] to [7], which is an antibody Fab, Fab', F(ab')$_2$, scFv, or dsFv.

BRIEF DESCRIPTION OF THE DRAWINGS

These and other objects and technical advantages of the present invention will be readily apparent from the following description of the preferred exemplary embodiments of the invention in conjunction with the accompanying drawings, in which:

FIG. 1 shows a gene sequence (SEQ ID NO:9) and an amino acid sequence (SEQ ID NO:7) of an H-chain variable region of an antibody recognizing GM1 ganglioside bound amyloid β-protein. CDR represents a complementarity determining region; and a signal sequence is a sequence of a signal portion.

FIG. 2 is shows a gene sequence (SEQ ID NO:10) and an amino acid sequence (SEQ ID NO:8) of an L-chain variable region of an antibody recognizing GM1 ganglioside-bound amyloid β-protein. CDR represents a complementarity determining region; and a signal sequence is a sequence of a signal portion.

FIG. 3 is a view showing a configuration of an expression vector in Example 1. FIG. 3A shows a configuration of an H-chain expression vector (BCMGSneo-H); and FIG. 3B shows a configuration of an L-chain expression vector (BCMGSneo-L).

FIG. 4 is a graph showing measurement results of the ThT assay in Example 2. In FIG. 4A, ■ denotes fluorescence when an Aβ solution was incubated with liposomes; and Δ denotes fluorescence when the Aβ solution was incubated with fAβ. It is shown that the fluorescence when the incubation was carried out in the presence of liposomes immediately increased without a lag phase and attained equilibrium hyperbolically. No increase in fluorescence was observed at all when the incubation was carried out in the absence of liposomes or fAβ (the case shown by (○)). FIG. 4B shows a semilogarithmical plot of the difference: F(∞)−F(t) versus incubation time (0-24 hrs). F(t) represents the increase in fluorescence as a function of time when Aβ was incubated with liposomes, and F(∞) was experimentally determined. FIG. 4C shows electron micrographs of the mixture incubated for 24 hours following addition of fAβ (upper micrograph) and the mixture incubated for 96 hours following addition of liposomes (lower micrograph). The bar indicates a length of 100 nm.

FIG. 5 shows results in Example 3. FIG. 5A shows electron micrographs of stained image. The left part shows an electron micrograph of a sample when GM1-containing liposomes (CH (cholesterol), SM (sphingomyelin), and GM1 (GM1 ganglioside)) and an Aβ solution were incubated and then stained with an antibody 4396C; a middle part shows an electron micrograph of a sample when GM1-containing liposomes and the Aβ solution were incubated and then stained with an antibody 4G8; and a right part shows an electron micrograph of a sample when liposomes lacking in GM1 (CH:cholesterol and SM: sphingomyelin) and the Aβ solution were incubated and then stained with the antibody 4396C. The results show that GM1-containing liposomes are labeled with the antibody 4396C (see left part), but not with the antibody 4G8 (see middle part). Furthermore, it is shown that the antibody 4396 does not recognize liposomes lacking in GM1 (see right part). The bar indicates a length of 50 nm. FIG. 5B shows results of the reactivity between the antibody 4396C and GM1 or soluble Aβ which was investigated by Western blotting. FIG. 5C shows results of the investigation on the reactivity between the antibody 4396C and an aggregated Aβ. FIG. 5C shows that serial sections of the cerebral cortex were immunolabeled with the antibody 4396C or the antibody 4G8 after treatment with formaldehyde, etc. It is shown that when the antibody 4G8 was used, neurotic plaques were strongly immunostained (right half part), but not at all immunostained when the antibody 4396C was used (left half part). Arrows indicate vessels in the serial sections.

FIG. 6A is a graph showing the results of the ThT assay in which an Aβ solution, GM1-containing liposomes and the antibody 4396C were concurrently incubated and the formation of amyloid fibrils was examined. The ratio of antibody 4396C molecules to Aβ molecules is 0.3:50 (Δ), 1.3:50 (○), and 4:50 (□), respectively. Furthermore, the ratio of antibody 4G8 molecules to Aβ molecules is 4:50 (◇). ■ denotes a result when the incubation was carried out without adding any antibodies. FIG. 6B shows results of immunoelectron micrograph of a mixture of synthetic Aβ$_{1-40}$ and 4G8, which were concurrently incubated for 24 hours following the addition of the GM1-containing liposomes. The sample was labeled with immunogold-labeled anti-mouse IgG. The bar indicates a length of 100 nm.

DETAILED DESCRIPTION OF THE INVENTION

Figure 7:
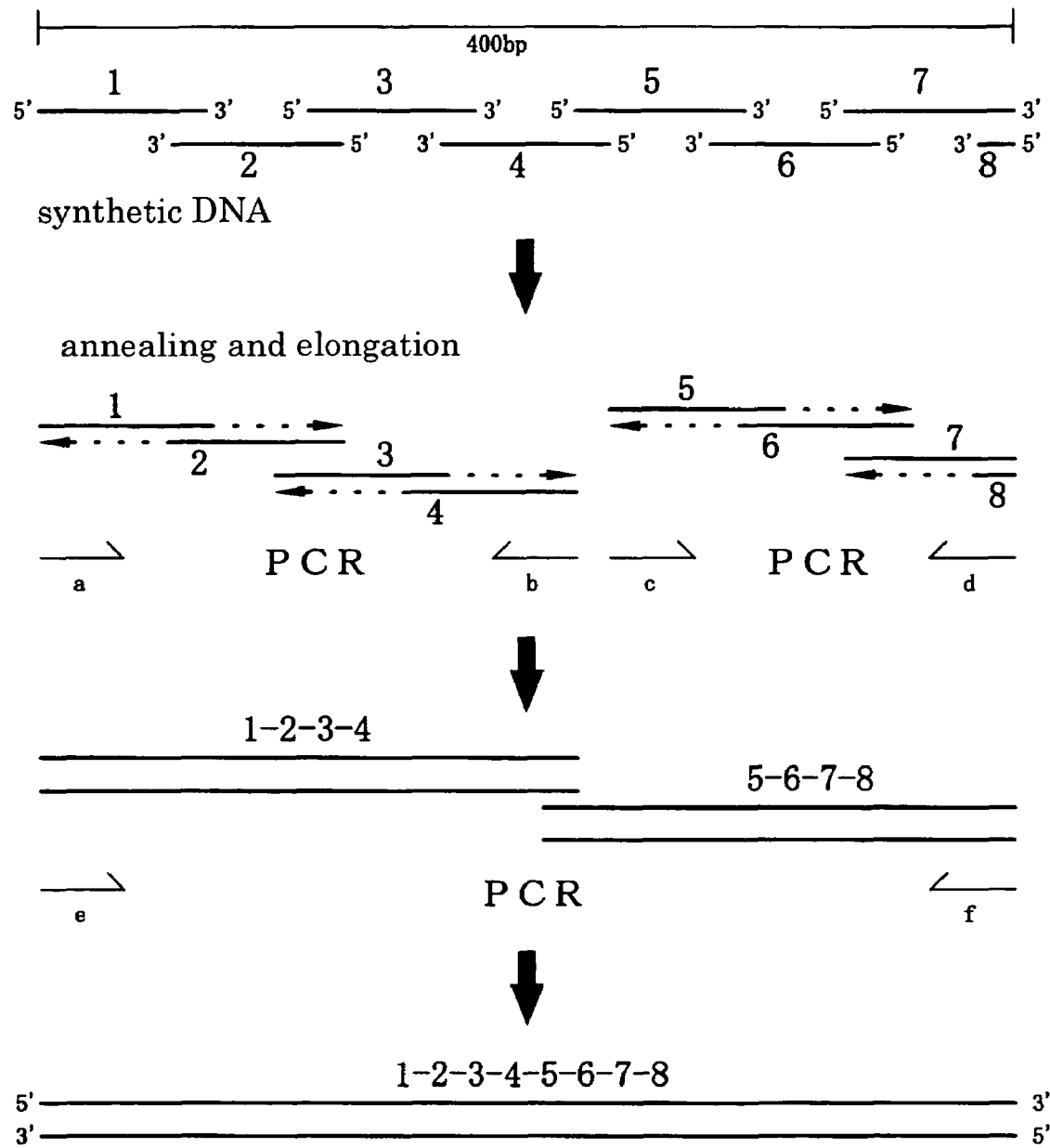
FIG. 7 is a schematic view showing a method for synthesizing DNA of the human CDR-grafted antibody variable region in Example 6.

Throughout the specification, the term "partial alteration of amino acid sequence" means that an amino acid sequence is altered by deletion or substitution of one to several amino acids constituting the amino acid sequence, or by addition or insertion of one to several amino acids, or by combination thereof.

A first aspect of the present invention relates to an antibody having an activity of recognizing GM1 ganglioside (GM1)-bound amyloid β-protein (Aβ) (GM1-Aβ) and inhibiting the formation of amyloid fibrils.

Antibodies of the present invention include an antibody of non-human animals such as mice, rats, etc., a chimeric antibody in which a part of a region has been substituted with that of different animals (including human), a humanized antibody, and a human antibody. Furthermore, a class of an antibody is not particularly limited. However, IgG class antibodies, for example, antibodies belonging to the human antibody subclasses, IgG1, IgG2, IgG3 and IgG4, are preferred.

For the variable region, a variable region of a mouse anti-GM1-Aβ antibody can be used. As the mouse anti-GM1-Aβ antibody, for example, a mouse anti-GM1-Aβ antibody obtained by immunizing a mouse with GM1-Aβ, as an antigen, purified from the brain of a patient with Alzheimer's disease may be used (for example, an antibody 4396 described in a paper may be used (K. Yanagisawa, J. McLaurin, M. Michikawa, A. Chakrabartty, Y. Ihara, FEBS Lett., 420, 43 (1997)).

It is preferable that the heavy chain variable region includes any one or more regions of a first region consisting of an amino acid sequence of SEQ ID NO. 1, a second region consisting of an amino acid sequence of SEQ ID NO. 2, and a third region consisting of an amino acid sequence of SEQ ID NO. 3. The first region, second region and third region herein correspond respectively to heavy chain CDR1, CDR2 and CDR3 of the antibody 4396. More preferably, the heavy chain variable region includes all of the first to third regions. Even more preferably, the heavy chain variable region includes the first region as CDR1, the second region as CDR2 and the third region as CDR3, respectively.

It is preferable that the light chain variable region includes any one or more regions of a fourth region consisting of the amino acid sequence of SEQ ID. NO. 4, a fifth region consisting of the amino acid sequence of SEQ ID. NO. 5, and a sixth region consisting of the amino acid sequence of SEQ ID. NO. 6. The fourth region, fifth region and sixth region herein correspond respectively to light chain CDR1, CDR2 and CDR3 of the antibody 4396. More preferably, the light chain variable region includes all of the fourth to sixth regions. Even more preferably, the light chain variable region includes the fourth region as CDR1, the fifth region as CDR2 and the sixth region as CDR3, respectively.

Instead of the amino acid sequences of the above-mentioned first to sixth regions, the amino acid sequences resulted from a partial alteration of these amino acid sequences can be used. However, alteration of the amino acid sequences can be carried out only in the range in which the antibody of the present invention has an activity of recognizing GM1-Aβ and inhibiting the formation of amyloid fibrils. As long as the antibody has an activity, the activity may be increased or reduced by the alteration of the amino acid sequence. The number of amino acids to be altered is preferably 30% or less, more preferably 20% or less, and even more preferably 10% or less, respectively with respect to the entire amino acids.

A preferable example of the antibody of the present invention may be an antibody including a heavy chain variable region, and a light chain variable region, wherein the heavy chain variable region has g) CDR 1 consisting of an amino acid sequence of SEQ ID NO. 1, or the amino acid sequence resulted from a partial alteration of SEQ ID NO. 1; h) CDR 2 consisting of an amino acid sequence of SEQ ID NO. 2, or the amino acid sequence resulted from a partial alteration of SEQ ID NO. 2; i) CDR 3 consisting of an amino acid sequence of SEQ ID NO. 3, or the amino acid sequence resulted from a partial alteration of SEQ ID NO. 3; and the light chain variable region has j) CDR 1 consisting of an amino acid sequence of SEQ ID NO. 4, or the amino acid sequence resulted from a partial alteration of SEQ ID NO. 4; k) CDR 2 consisting of an amino acid sequence of SEQ ID NO. 5, or the amino acid sequence resulted from a partial alteration of SEQ ID NO. 5; and 1) CDR 3 consisting of an amino acid sequence of SEQ ID NO. 6, or the amino acid sequence resulted from a partial alteration of SEQ ID NO. 6. Examples of the amino acid sequence of the heavy chain variable region and the light chain variable region of the antibody may include amino acid sequences of SEQ ID NO. 7 and SEQ ID NO. 8, respectively. In this case, an amino acid sequence configured by excluding the signal part may be used. Note here that the amino acid sequences of SEQ ID NO. 7 and SEQ ID NO. 8 correspond respectively to the amino acid sequences of the heavy chain variable region and the light chain variable region of the antibody 4396.

The antibody of the present invention includes a humanized antibody. The humanized antibody herein denotes an antibody whose structure is similar to a human antibody, and includes a human chimeric antibody in which only a constant region is substituted with that of a human antibody, and a human CDR-grafted antibody in which the constant region and a part of the region other than a CDR (complementarity determining region) existing in the variable region is substituted with that of a human antibody (P. T. Johons et al., Nature 321,522 (1986)).

A human chimeric antibody can be prepared by substituting a constant region of an antibody having, for example, a structure of a heavy chain variable region and/or a structure of a light chain variable region (for example, an IgG class mouse anti-GM1-Aβ antibody (antibody 4396C) prepared from an antibody 4396 by a class switch technology of genetic engineering (M. M. Bending, S. T. Jones, in Antibody Engineering, J. McMafferty, H. R. Hoogenboon and D. J. Chiswell Eds. (IRL Press, 1996), pp.147-165) for the constant region of the human antibody. The constant region of a human antibody, which is conventionally known, can be used.

Hereinafter, an example of a method for preparing a human chimeric antibody will be mentioned.

Firstly, mRNA is extracted from a hybridoma producing a mouse anti GM1-Aβ antibody and a cDNA is synthesized by a conventional technique. The synthesized cDNA is incorporated into a vector, and a cDNA library is constructed. From this cDNA library, a vector containing an H-chain gene and an L-chain gene is selected by using an H-chain gene fragment and L-chain gene fragment as probes. By sequencing an insertion sequence of the selected vector, gene sequences of the H-chain variable region and L-chain variable region are determined. Based on the thus obtained sequence data, a DNA encoding the H-chain variable region is prepared by way of a chemical synthesis, biochemical cleavage/rebinding, and the like. The obtained DNA encoding the H-chain variable region is ligated with a DNA encoding a human H-chain constant region and incorporated into an expression vector to form an H-chain expression vector. As an expression vector, for example, a SV40 virus based vector, an EB virus based vector, a BPV (papillomavirus) based vector, etc. can be used, but the expression vector is not necessarily limited thereto. In the meanwhile, an L-chain expression vector is prepared by a similar method. A host cell is cotransformed with these H-chain expression vector and L-chain expression vector. As a host cell, a CHO (Chinese hamster ovary) cell (A. Wright & S. L. Morrison, J. Immunol. 160, 3393-3402 (1998)), a SP2/0 (mouse myeloma) cell (K. Motmans et al., Eur. J. Cancer Prev. 5,512-519 (1996), R. P. Junghansetal., Cancer Res. 50, 1495-1502 (1990)), and the like are suitably used. Furthermore, for transformation, the lipofectin method (R. W. Malone et al., Proc. Natl. Acad. Sci. USA 86, 6077 (1989); P. L. Felgner et al., Proc. Natl. Acad. Sci. USA 84,7413

(1987)), an electroporation method, a calcium phosphate method (F. L. Graham & A. J. van der Eb, Virology 52, 456-467 (1973)), a DEAE-Dextran method, and the like are suitably used.

Then, a human chimeric antibody is obtained from the inside of the cell or a culture medium of this transformant. The antibody can be isolated and purified by appropriately combining methods, for example, centrifugation, ammonium sulfate fractionation, salting out, ultrafiltration, affinity chromatography, ion-exchange chromatography, gel-filtration chromatography, and the like.

On the other hand, a human CDR-grafted antibody can be prepared by, for example, the following method.

Firstly, by the method mentioned with respect to the method for producing a chimeric antibody, an amino acid sequence of the H-chain variable region and the L-chain variable region of a mouse anti-GM1-Aβ antibody and a base sequence encoding thereof are determined. In addition, the amino acid sequence and a base sequence of each CDR region are also determined.

As specific base sequences of the CDRs, for example, for CDR1, CDR2 and CDR3 of the H chain, sequences shown in SEQ ID NO. 11, SEQ ID NO. 12, and SEQ ID NO. 13 can be used, respectively; and for CDR1, CDR2 and CDR3 of the L chain, sequences shown in SEQ ID NO. 14, SEQ ID NO. 15 and SEQ ID NO. 16 can be used, respectively.

Then, FRs (framework regions) existing around the CDR region are selected. For selecting FRs, substantially three methods can be employed. The first method uses a human antibody frame such as NEWM, REI, and the like, whose three-dimensional structures have been clarified (Riechmann L. et al., Nature 332, 323-3Z7 (1988); Tempst, PR. et al., Protein Engineering 7, 1501-1507 (1994); Ellis J H. et al., J. Immunol 155, 925-937 (1995)). The second method selects a human antibody variable region having the highest homology to the target mouse antibody variable region from the database and uses the FR thereof (Queen C. et al., Proc Natl Acad Sci USA 86, 10029-10033 (1989); Rozak M J. et al., J Biol Chem 271, 22611-22618 (1996); Shearman C W. et al., J. Immunol 147, 4366-4373 (1991)). The third method selects amino acid used most commonly in the FR of a human antibody (Sato K. et al., Mol Immunol 31, 371-381 (1994); Kobinger F. et al., Protein Engineering 6, 971-980 (1993); Kettleborough C A. et al., Protein Engineering 4, 773-783 (1991)). In the present invention, any of these methods can be used.

Note here that in the present invention, an amino acid sequence resulted from a partial alteration of the selected human FR can be also used as an amino acid sequence of FR as long as the finally obtained human CDR-grafted antibody has an activity of recognizing GM1-Aβ and controlling the formation of amyloid fibrils. In particular, in the case where a part of the amino acids of the selected human FR is altered into the amino acids of FR of the antibody from which CDR is derived, the possibility of maintaining the characteristics of the antibody is high. The number of amino acids to be altered is preferably 30% or less, more preferably 20% or less, and even more preferably 10% or less, respectively with respect to the entire FRs.

Then, by combining the FR, which is selected by any of these methods, with the CDR, DNAs encoding the H-chain variable region and the L-chain variable region are designed. Based on the design, the DNAs encoding the H-chain variable region and the DNA encoding the L-chain variable region are prepared by way of a chemical synthesis, biochemical cleavage/rebinding, and the like. Then, the DNA encoding the H-chain variable region together with a DNA encoding a human immunoglobulin H-chain constant region are incorporated into an expression vector to form an H-chain expression vector. Similarly, the DNA encoding the L-chain variable region together with a DNA encoding a human immunoglobulin L-chain constant region are incorporated into an expression vector to form an L-chain expression vector. As an expression vector, for example, a SV40 virus based vector, an EB virus based vector, a BPV (papillomavirus) based vector, etc. can be used, but the expression vector is not necessarily limited thereto.

A host cell is cotransformed with the H-chain expression vector and the L-chain expression vector prepared by the above-mentioned method. As the host cell, a CHO (Chinese hamster ovary) cell (A. Wright & S. L. Morrison, J. Immunol. 160, 3393-3402 (1998)), a SP2/0 (mouse myeloma) cell (K. Motmans et al., Eur. J. Cancer Prev. 5,512-519 (1996), R. P. Junghans et al., Cancer Res. 50, 1495-1502 (1990)), and the like are suitably used. Furthermore, for transformation, the lipofectin method (R. W. Malone et al., Proc. Natl. Acad. Sci. USA 86, 6077 (1989); P. L. Felgner et al., Proc. Natl. Acad. Sci. USA 84,7413 (1987)), an electroporation method, a calcium phosphate method (F. L. Graham & A. J. van der Eb, Virology 52, 456-467 (1973)), a DEAE-Dextran method, and the like are suitably used. Then, a human CDR-grafted antibody is obtained from the inside the cell or a culture medium of this transformant. The antibody can be isolated and purified by appropriately combining methods, for example, centrifugation, ammonium sulfate fractionation, salting out, ultrafiltration, affinity chromatography, ion-exchange chromatography, gel-filtration chromatography, and the like.

Based on the antibody of the present invention or based on the sequence information of a gene encoding the antibody, an antibody fragment can be prepared. Examples of the antibody fragments include Fab, Fab', F(ab')$_2$, scFv, dsFv, and the like.

Fab is obtained by digesting IgG with papain in the presence of systein. Fab is an antibody fragment having a molecular weight of about 50,000 and includes the L-chain and H-chain variable regions and an H-chain fragment composed of a $C_H 1$ domain and a part of a hinge portion. In the present invention, Fab can be obtained by digesting the above-mentioned antibody with papain. Furthermore, Fab can be also prepared from a transformant formed by using a vector in which DNAs encoding a part of the H chain and the L chain are incorporated.

Fab' is an antibody fragment having a molecular weight of about 50,000, which can be obtained by cleaving the disulfide bond between the H chains of F(ab')$_2$ mentioned below. In the present invention, Fab' is prepared by digesting the above-mentioned antibody with pepsin and cleaving the disulfide bond by using a reducing agent. Furthermore, similar to Fab, Fab' can be also prepared by genetically engineering using a DNA encoding Fab'.

F(ab')$_2$ is obtained by digesting IgG with pepsin. F(ab')$_2$ is a fragment having a molecular weight of about 100,000, in which F(ab')s including the L-chain and the H-chain variable regions and an H-chain fragment composed of a $C_H 1$ domain and a part of a hinge portion are bonded to each other via the disulfide bond. In the present invention, F(ab')$_2$ can be obtained by digesting the above-mentioned antibody with pepsin. Furthermore, similar to Fab, F(ab')$_2$ can be also prepared by genetically engineering by using a DNA encoding F(ab')$_2$.

scFv is an antibody fragment formed in a form of a single-strand conformation by linking two chains of Fv, which is composed of the H-chain variable region and the L-chain variable region, in a manner that the C-terminal of one chain is linked to the N-terminal of the other chain via a suitable peptide linker. As a peptide linker, for example, (GGGGS)$_3$, etc. having high flexibility can be used. For example, by using DNAs encoding the H-chain variable region and the L-chain variable region and a DNA encoding a peptide linker, a DNA encoding scFv antibody is constructed and incorporated into an appropriate vector to form a transformant. From the transformant, scFv can be also prepared.

dsFv is a Fv fragment in which Cys residues are introduced into a suitable positions of the H-chain variable region and the L-chain variable region, and the H-chain variable region and the L-chain variable region are stabilized via the disulfide bond. The position into which Cys residue of each chain is introduced can be determined based on the conformation predicted by molecule modeling. In the present invention, the conformation is predicted from, for example, the amino acid sequences of the H-chain variable region and L-chain variable region. Based on such prediction, DNAs encoding the H-chain variable region and the L-chain variable region, in which a mutant is introduced, are constructed, respectively and incorporated into a suitable vector to form a transformant. From the transformant, dsFv can be also prepared.

Note here that antibody fragments can be multimerized by linking scFv antibody, dcFv antibody, and the like by using a suitable linker, or by fusing streptavidin thereto.

By fusing or binding a low molecular compound, protein, target material and the like, to the antibody (including an antibody fragment) of the present invention, a fused antibody or a labeled antibody can be constructed. As a labeled material, a radioactive material such as $^{125}$I, peroxidase, β-D-galactosidase, microperoxidase, horseradish peroxidase (HRP), fluorescein isothiocyanate (FITC), rhodamine isothiocyanate (RITC), alkaline phosphatase, biotin, and the like can be used.

A second aspect of the present invention relates to a DNA encoding the antibody of the first aspect of the present invention. That is to say, the second aspect of the present invention relates to a DNA of an antibody having an activity of recognizing GM1-Aβ and inhibiting the formation of amyloid fibrils. In particular, the DNA includes DNAs encoding a human chimeric antibody and a human CDR-grafted antibody, which have the above-mentioned activity, and a DNA encoding an antibody fragment. The present invention also includes DNAs encoding the H chain or the L chain of these antibodies or antibody fragments. Furthermore, the present invention includes DNAs encoding the H-chain variable region or the L-chain variable region of these antibodies or antibody fragments. In this case, the DNA may be configured excluding a signal portion. A concrete example of the DNA sequence of the H-chain variable region includes a sequence shown in SEQ ID NO. 9. Furthermore, an example of the DNA sequence of the specific L-chain variable region includes a sequence shown in SEQ ID NO. 10.

Furthermore, the present invention includes a sequence of a gene encoding a variable region CDR of an antibody having an activity of recognizing GM1-Aβ and inhibiting the formation of amyloid fibrils. Concrete examples of such a sequence includes: a sequence encoding an amino acid sequence of SEQ ID NO. 1 (for example, a sequence of SEQ ID NO. 11), a sequence encoding an amino acid sequence of SEQ ID NO. 2 (for example, a sequence of SEQ ID NO. 12), a sequence encoding an amino acid sequence of SEQ ID NO. 3 (for example, a sequence of SEQ ID NO. 13), a sequence encoding an amino acid sequence of SEQ ID NO. 4 (for example, a sequence of SEQ ID NO. 14), a sequence encoding an amino acid sequence of SEQ ID NO. 5 (for example, a sequence of SEQ ID NO. 15), or a sequence encoding an amino acid sequence of SEQ ID NO. 6 (for example, a sequence of SEQ ID NO. 16). The above-mentioned DNA can be prepared by way of a chemical synthesis, biochemical cleavage/rebinding, and the like, and can be used in, for example, preparing antibodies or antibody fragments having an activity of recognizing GM1-Aβ and inhibiting the formation of amyloid fibrils.

The DNA of the present invention is incorporated into a vector, then by using this vector, a host cell can be transformed. Furthermore, in the DNAs of the present invention, a DNA encoding an antibody heavy chain (or a heavy chain variable region) is incorporated into one vector and a DNA encoding an antibody light chain (or a light chain variable region) is incorporated into another vector to form two expression vectors. Then, a host cell may be cotransformed with the two resultant expression vectors. Furthermore, in the DNAs of the present invention, the DNA encoding the antibody heavy chain (or the heavy chain variable region) and the DNA encoding the antibody light chain (or the light chain variable region) are incorporated into one same vector, and then by using this vector, a host cell may be transformed.

Kinds of vectors to be used are not particularly limited as long as the DNA of the present invention can be incorporated in a manner capable of expression, and can be in deed expressed in a host cell.

Kinds of host cells are not particularly limited as long as they can be transformed by a vector to be used and can express the DNA of the present invention. For example, bacteria such as *Escherichia coli*, yeast such as *Saccharomyces cerevisiae*, and an animal cell such as a COS cell, a CHO cell, etc. can be used.

By cultivating a transformant, an antibody or antibody fragment having an activity of recognizing GM1-Aβ and inhibiting the formation of amyloid fibrils can be produced (expressed) in a cell or a culture medium. Then, by collecting the produced antibody (including antibody fragment), the antibody of the first aspect of the present invention can be obtained. The obtained antibody can be isolated and purified by appropriately combining methods, for example, centrifugation, ammonium sulfate fractionation, salting out, ultrafiltration, affinity chromatography, ion-exchange chromatography, gel-filtration chromatography, and the like.

Whether or not the antibody of the present invention has an activity of recognizing GM-Aβ can be confirmed by observing the binding property between a subject antibody and GM1-β when the subject antibody is brought into contact with GM1-Aβ. For example, a lipid membrane containing GM1 ganglioside (GM1)-bound amyloid β-protein (Aβ) (GM1-Aβ) is formed and the binding property of GM1-Aβ to the subject antibody is observed. Furthermore, a lipid membrane containing GM1 is prepared, and a solution containing Aβ and the subject antibody are concurrently brought into contact with (added into) the prepared lipid membrane, and thereby the binding capacity of the subject antibody to GM1-Aβ may be examined. The lipid membrane containing GM1-Aβ can be prepared by bringing (adding) a solution containing Aβ into contact with the lipid membrane containing GM1. In this case, it is preferable that contacting between the lipid membrane containing GM1 and the solution containing Aβ is carried out for a short time. More preferably, contacting between them can be carried out instantly.

The lipid membrane containing GM1 is not particularly limited as long as it contains GM1 and a lipid material as components. However, a lipid membrane including sphingomyelin as a lipid component is preferably used. Furthermore, a lipid membrane further including cholesterol is preferably used. The configuration of such lipid membranes is similar to that of the neuron membrane in the brain in which amyloid fibrils are formed. Thus, by using the lipid membrane having such a configuration, it is possible to confirm that the antibody of the present invention is an antibody capable of effectively inhibiting the formation of amyloid fibrils in vivo.

As GM1, for example, a commercially available material (a material available from Wako Pure Chemical Industries Ltd., Osaka, Japan, etc.) can be used. As Aβ, for example, commercially available $Aβ_{1-40}$ (Lot. 501001 available from Peptide Inst. Osaka, Japan; Lot. 519599 available from Bachem A G, Switzerland, etc.) can be used.

The lipid membrane containing GM1 can be prepared in the form of liposomes. Furthermore, the lipid membrane containing GM1 can be used in a state biding to an insoluble support, for example, beads made of resin such as polystyrene resin, polycarbonate resin, silicon resin, nylon resin, etc., glass, or the like, and a microplate.

Note here that if the formation of amyloid fibrils can be inhibited when the subject antibody is brought into contact with GM1-Aβ in the presence of Aβ, it can be confirmed that the subject antibody binds to GM1-Aβ and has an activity of inhibiting the formation of amyloid fibrils.

A lipid membrane containing GM1-Aβ can be also used for screening a compound having a binding property with respect to GM1-Aβ. That is to say, a method for screening a compound having a binding property with respect to GM1-Aβ can be achieved by including the following steps:

1) a step for bringing a sample into contact with a lipid membrane containing GM1 ganglioside-bound amyloid β-protein, and 2) a step of collecting a compound binding to the lipid membrane.

In the step 1), a lipid membrane containing GM1 ganglioside bound amyloid β-protein (GM1-Aβ) can be used in the form of liposomes or in a state binding to an insoluble support (for example, a microplate). In the case of using the lipid membrane in the form of liposomes, a compound bound to GM1-Aβ can be isolated and purified by centrifugation in the step 2), and thereby a target compound can be obtained. Furthermore, in the case where a candidate compound is an antibody, GM1-Aβ-containing liposomes including calcein is used as a lipid membrane of the step 1), and an amount of calcein, released from the liposomes when it is ruptured by the effect of the complement system, can be measured, thereby determining a binding activity of the candidate compound to GM1-Aβ. On the other hand, in the case where a lipid membrane bound to an insoluble support is used, when a candidate compound is an antibody, it is possible to measure the binding activity of the candidate compound to GM1-Aβ can be measured by EIA, ELISA, and the like.

Instead of the above-mentioned step 1), the following steps 1-1) and 1-2) may be carried out:

1-1) a step of bringing a lipid membrane containing GM1 ganglioside into contact with amyloid β-protein to produce GM1 ganglioside-bound amyloid β-protein; and 1-2) a step of bringing a sample into contact with the lipid membranes.

The lipid membrane containing GM1 ganglioside (GM1) can be brought into contact with amyloid β-protein (Aβ) in the step 1-1) by, for example, adding a solution containing Aβ into a lipid membrane-dispersing solution. Furthermore, it can be done by bringing a solution containing Aβ into contact with the lipid membrane fixed on a solid phase (for example, a lipid membrane bound to a microplate).

The above-mentioned steps 1-1) and 1-2) may be carried out substantially at the same time. That is to say, a method for screening a compound having a binding property with respect to GM1-Aβ can be configured by including the following step:.

1') a step of adding amyloid β-protein and a sample into a solution that contains a lipid membrane containing GM1 ganglioside.

In addition to the above-mentioned steps, by carrying out a step of confirming that the formation of amyloid fibrils can be inhibited (step 3), it is possible to confirm that a compound selected by the screening method has a binding property with respect to GM1-Aβ and has an activity of inhibiting the formation of amyloid fibrils. For example, a collected compound having binding property with respect to GM1-Aβ is allowed to coexist in the environment in which amyloid fibrils are formed, and thereby the influence and effect of the compound on the formation of amyloid fibrils are confirmed. Furthermore, when the step 1) or 1-2) is carried out, the step 3) may be carried out by adding Aβ together with a sample and observing the formation of amyloid fibrils.

The compound selected by the above-mentioned screening method has a binding property with respect to GM1-Aβ. Therefore, the compound can be used for inhibiting or preventing Aβ from being polymerized to GM1-Aβ and from amyloid fibrils being formed.

As a sample to be screened, natural or synthetic protein, peptide, antibody (including an antibody of the present invention), cell extract, culture supernatant, and the like, can be used.

The use of the antibody (including an antibody fragment) of the first aspect of the present invention makes it possible to configure a method for screening a compound having an activity of binding to GM1-Aβ.

That is to say, the present invention also provides a method for screening a compound having an activity of binding to GM1-Aβ. The method includes the following steps:

i) a step of selecting a first compound binding to an antibody or an antibody fragment according to the first aspect of the present invention; and ii) a step of selecting a second compound biding to the first compound. Also in this screening method, by including a step of confirming that the formation of amyloid fibrils can be inhibited, it is possible to confirm that the compound selected by the screening method has an activity of binding to GM1-Aβ and inhibiting the formation of amyloid fibrils.

In the step i), the binding property between an antibody or an antibody fragment and a sample is examined, and a first compound having binding property is selected. As the sample herein, as in the case mentioned above, natural or synthetic protein, peptide, antibody (including an antibody of the present invention), cell extract, culture supernatant, and the like, can be used.

In the step i), an antibody to be used can be fixed on a solid phase and a sample can be brought into contact with the fixed antibody. On the contrary, the side of the sample may be fixed on a solid phase.

By labeling an antibody to be used in advance, facilitation of selection (detection) and enhancement of the selection (detection) efficiency are achieved. For labeling, a radioactive material such as $^{125}I$, and an enzyme such as peroxidase, β-D-galactosidase, etc. can be used. Furthermore, by using a secondary antibody recognizing an antibody to be used, the selection (detection) efficiency may be enhanced.

The antibody (including an antibody fragment) of the first aspect of the present invention may be used for screening a compound binding to an antibody that recognizes GM1-Aβ. That is to say, a method for screening a compound binding to an antibody that recognizes GM1-Aβ can be configured, and the method includes the following steps A) and B):

A) a step of bringing a sample into contact with the antibody of the present invention; and B) a step of collecting a compound binding to the antibody.

As the sample herein, natural or synthetic protein, peptide, cell extract, culture supernatant, and the like, can be used.

Furthermore, a method for screening a compound binding to an antibody that recognizes GM1-Aβ can be configured, and the method including the following steps:

C) a step of predicting a conformation of a variable region of the antibody of the present invention; and D) a step of selecting a compound having a conformation that is complementary to the predicted conformation.

The conformation of a variable region of an antibody can be predicted by a NMR (nuclear magnetic resonance) method (Wuthrich, K.: NMR of Protein and Nucleic Acids, John Wiley & Sons, New York, 1986), X ray crystallography (Blundell, T. L. and John, L. N.: Protein Crystallography, Academic Press, Oxford, pp.1-565, 1976, McPherson, A.: Preparation and Analysis of Protein Crystals, John Wiley & Sons, New York, pp.1-371,1982; Masaaki Matsushima et al.: Study method of Protein Engineering, chapter 7, Conformation Analysis, Hirokawa Shoten, Tokyo, 160-200, 1990), and the like.

An example of a candidate compound in the step D) can include a natural protein, natural peptide, natural high molecular compound, and the like, which are extracted from plant, animal, and bacteria, etc., as well as synthetic protein, synthetic peptide, synthetic high molecular compound, synthetic low molecular compound, and the like.

Since the compound obtained by the above-mentioned screening method has an activity of binding to an anti-GM1-Aβ antibody, it is thought that it can cause the production of an anti-GM1-Aβ antibody when it is administered to a living body. That is to say, it can act on the immunodefense mechanism of the living body to produce an anti-GM1-Aβ antibody. As a result, it is thought that by the effect of this antibody, Aβ can be inhibited from being polymerized to GM1-Aβ formed in the living body and the formation of amyloid fibrils can be inhibited. Therefore, it is thought that by using the compound, Alzheimer's disease can be prevented or treated. In other words, by using the compound, a method for preventing and treating Alzheimer's disease can be provided. Furthermore, drugs, i.e., vaccines or therapeutic drugs for Alzheimer's disease, which contain the compound as an effective component, can be created. On the other hand, since the lipid membrane containing GM1-Aβ, which is used for the above-mentioned screening method etc., is also recognized by the anti-GM1-Aβ antibody, when it is administered to the living body, it can cause the production of an anti-GM1-Aβ antibody. Therefore, also the lipid membrane can be used for the same purpose.

In drug formulation, pharmaceutically acceptable other components (for example, physiologic saline, excipient, preservative) may be contained. Furthermore, drugs can be formulated in various forms, for example, in a form of capsule, syrup, tablet, granule, etc. Drugs can be administered via oral administration, parenteral administration (intravenous-, intra-arterial-, subcutaneous-, intramuscular-, intraperitoneal injections, and the like).

A dose is different dependent upon symptom, age, weight, of a patient etc. However, a person skilled in the art can select and set the suitable dose.

On the other hand, since the antibody (including antibody fragment) of the present invention can specifically bind to GM1-Aβ and inhibit the formation of amyloid fibrils, it is useful for diagnosis, prevention and treatment for Alzheimer's disease. That is to say, it is thought that by using the antibody of the present invention, diagnosis, prevention or treatment for Alzheimer's disease can be carried out. In other words, by using the antibody of the present invention, methods for diagnosing, preventing and treating Alzheimer's disease can be provided. Furthermore, by using an antibody of the present invention, drugs (diagnosis drugs, preventive drugs or therapeutic drugs) for Alzheimer's disease can be created. Herein, when a humanized antibody of the present invention is used, even in a case where the antibody is administered to a human body, it is recognized as a human protein. Therefore, since it is not likely to be excreted from the circulatory system and an allergy reaction is not likely to occur, it can be thought that the antibody can be used as a suitable diagnosis drug, etc. On the other hand, a compound having binding property with respect to GM1-Aβ, which is selected in the above-mentioned screening method, can be used for methods for diagnosing, preventing and treating Alzheimer's disease. Furthermore, by using the compound, drugs (diagnosis drugs, preventive drugs or therapeutic drugs) for Alzheimer's disease can be created.

For the drugs of the present invention, pharmaceutically acceptable other components (for example, physiologic saline, excipient, preservative) can be contained. Furthermore, drugs can be formulated in various forms, for example, in a form of capsule, syrup, tablet, granule and the like, and it can be administered via oral administration, parenteral administration (intravenous-, intra-arterial-, subcutaneous-, intramuscular-, intraperitoneal injections, and the like). Note here that drugs maybe formulated combining plural antibodies of the present invention.

A dose is different dependent upon symptom, age, weight, of a patient etc. However, a person skilled in the art can select and set the suitable dose.

EXAMPLE 1

Preparation of IgG Antibody 1-1) Determination of Gene Sequence of Variable Region A gene sequence of a variable region of a hybridoma (hereinafter, "Aβ1-42C" will be referred to) producing the antibody (antibody 4396) described in the above-mentioned paper (K. Yanagisawa, J. McLaurin, M. Michikawa, A. Chakrabartty, Y. Ihara, FEBS Lett., 420, 43 (1997)) was determined by the following procedure. Note here that Aβ$_1$-42C is a hybridoma prepared using GM1-Aβ purified from the brain as an immunogen and the antibody 4396 is an IgM class antibody which specifically recognizes GM1-Aβ.

Firstly, by using "ZAPcDNA kit" (Stratagene Corporate), cDNA library of Aβ1-42C was constructed. The construction method followed the protocol of the kit. Aβ1-42C was cultivated in DMEM/10% FCS and poly A$^+$RNA was prepared from about 3×10$^7$ cells. After a first chain cDNA was synthesized from 5 μg of A$^+$RNA, a second chain cDNA was synthesized. Then, a linker (having EcoRI and XhoI sites) was ligated thererto, and the cDNA was incorporated into the EcoRI/XhoI sites of "Uni-ZAP XR vector" of the kit. Then, the vector was packaged in a VCMG13 phage by using "ZAPcDNA Gigapack III Gold Cloning Kit" (Stratagene Corporate).

By infecting the phage with E. coli/XL-I blue in "ZAPcDNA Gigapack III Gold Cloning Kit," plaques were formed in a culture medium. Thereafter, plaque hybridization was carried out as follows. As a probe, a μ-chain gene (H-chain constant region) fragment and a λ-chain gene (L-chain constant region) fragment, which had been proliferated by PCR in advance, were used.

On a NZY culture medium in which plaques were formed, "Hybond-N+membrane" (Amersham) was loaded, and the plaques were transcribed on a membrane. Thereafter, the membrane was treated with 1.5M NaCl/0.5M NaOH for two minutes, with 1.5M NaCl/0.5M Tris-HCl (pH7.5) for five minutes, and with 0.2M Tris-HCl (pH7.5)/2×SSC for 30 seconds, followed by air drying. DNA probe was labeled using "ECL direct nucleic acid labeling and detection systems" (Amersham). This labeled probe and membrane were incubated at 42° C. for 4 hours, then washed, and immersed in a chromogenic substrate. Then, the membrane was brought into close contact with "Hyper-film ECL" (Amersham) and exposed for five minutes. Based on the film, positive plaques were isolated from the culture medium. After selecting positive phages, by using "Uni-ZAP XR vector cloning kit" (Stratagene Corporate), the positive phages were infected with E. coli/SOLR strain attached to the kit, and phagemids were cleaved from "Uni-ZAP XR DNA" in the phage. From E. coli/SOLR strain, phagemid DNA was purified by the alkaline SDS method. Then, the insertion sequence in the phagemid DNA was determined by the dideoxy method.

As a result, these DNAs included a μ-chain gene (H-chain constant region) and a λ-chain gene (L-chain constant region), respectively. Then, from each DNA, gene sequences and amino acid sequences of the H-chain variable region ($V_H$) and L-chain variable region ($V_L$) were determined respectively as shown in FIGS. 1 and 2. In FIGS. 1 and 2, CDR represents a complementarity determining region. An amino acid sequence of the H-chain variable region is shown in SEQ ID NO: 7 (sequence from positions 1 to 19 encodes a signal sequence); a base sequence encoding the amino acid sequence is shown in SEQ ID NO. 9 (sequence from positions 1 to 57 encodes a signal sequence); an amino acid sequence of the L-chain variable region is shown in SEQ ID NO. 8 (sequence from position 1 to 19 encodes a signal sequence); and a base sequence encoding the amino acid sequence is shown in SEQ ID NO. 10 (sequence from position 1 to 57 encodes a signal sequence). Furthermore, in the H-chain variable region, an amid acid sequence of CDR 1 is shown in SEQ ID NO. 1; a base sequence encoding the amino acid sequence is shown in SEQ ID NO. 11; an amid acid sequence of CDR 2 is shown in SEQ ID NO. 2; a base sequence encoding the amino acid sequence is shown in SEQ ID NO. 12; an amid acid sequence of CDR 3 is shown in SEQ ID NO. 3; and a base sequence encoding the amid acid sequence is shown in SEQ ID NO. 13. Similarly, in the L-chain variable region, an amino acid sequence of CDR 1 is shown in SEQ ID NO. 4; a base sequence encoding the amid acid sequence is shown in SEQ ID NO. 14; an amino acid sequence of CDR 2 is shown in SEQ ID NO. 5; a base sequence encoding the amid acid sequence is shown in SEQ ID NO. 15; an amino acid sequence of the CDR 3 is shown in SEQ ID NO. 6; and a base sequence encoding the amid acid sequence is shown in SEQ ID NO. 16.

1-2) Preparation of H-Chain Expression Vector and L-Chain Expression Vector

The above-mentioned H-chain variable region DNA derived from the antibody 4396 was ligated to an H-chain constant region DNA of a mouse IgG2a antibody and incorporated into an expression vector "BCMGS Neo Vector" (Hajime Toriyama, Bovine papillomavirus vector, Experimental Medicine (supplementary volume), Genetic Engineering Handbook published by Masami Muramatsu and Hirohito Okayama, YODOSHA CO., LTD., pp. 297-299 (1991)) (cleaved with XhoI and NotI sites) to form an H-chain expression vector (BCMGSneo-H) (see FIG. 3A). Similarly, the above-mentioned L-chain variable region DNA derived from the antibody 4396 was ligated to an L-chain constant region DNA of the mouse IgG2 a antibody, incorporated into the expression vector "BCMGS Neo vector" (cleaved with XhoI and NotI sites) to form an L-chain expression vector (BCMGSneo-L) (FIG. 3B).

1-3) Transfection

The H-chain expression vector and the L-chain expression vector were concurrently transfected into a CHO (Chinese hamster ovary) cell by the lipofectin method, cultivated at 37° C. for 12 hours, transplanted into a 96-well plate, and selected in DMEM/10% FCS containing 500 μg/ml of G-418.

The amount of IgG in the culture medium was measured as follows. An anti-mouse γ-chain (Medical & Biological Laboratories Co., Ltd.: code 303G) was diluted with PBS to 10 μg/ml, dispensed into a polystyrene microplate in an amount of 100 μl to each well, and sensitized at 4° C. over night. Then, blocking was carried out by using 5% BSA/5% sucrose/PBS at 4° C. over night. 100 μl of sample was reacted at 37° C. for one hour, followed by washing with PBS/0.05% Tween 20. After washing, 4000× diluted peroxidase-labeled anti-mouse IgG (Medical & Biological Laboratories Co., Ltd.: code 330) was reacted at 37° C. for one hour, followed by washing with PBS/0.05% Tween 20. After washing, 100 μl of enzyme-substrate solution was dispensed and reacted at room temperature for 15 minutes. Then, 100 μl of 2N sulfuric acid was dispensed to each well, and $A_{492}$ was measured. For control, mouse sera (amount of IgG: 200 ng/ml, 20 ng/ml, 2 ng/ml, and 0.2 ng/ml) were used. Thus, a clone exhibiting the largest amount of expression was selected and the culture supernatant thereof was collected. From the collected culture supernatant, an antibody was purified by using a protein A agarose column. The resultant antibody was defined as an antibody 4396C.

EXAMPLE 2

Investigation of Binding Property of Antibody 4396C to GM1-Aβ

In order to clarify the molecular mechanism of the initiation of the amyloid fibril formation by GM1, by using GM1-containing liposomes, a kinetic analysis and a morphologic analysis were carried out.

2-1) Preparation of Aβ Solution

Firstly, synthetic $Aβ_{1-40}$ (Peptide Inst., Osaka, Japan; Lot. 501001) was dissolved in 0.002% ammonia solution at about 500 μM and the solution was centrifuged at 100,000 rpm for 3 hours (TLA 120.0 Rotor, Optima T L, Beckman, Calif., USA). Only the upper two-thirds of the supernatant was collected and the concentration of Aβ was determined. Aliquotes of the Aβ solution were stored at −80° C. until use. Immediately before use, the Aβ solution was dissolved and diluted with physiological Tris buffer (TBS: 150 mM NaCl and 10 mM Tris-HCl, pH7.4) to an optimal concentration.

2-2) Preparation of GM1-Containing Liposomes

Cholesterol, sphingomyelin (Sigma-Aldrich, St. Louis, Mo., USA) and GM1 (Wako Pure Chemical Industries Ltd., Osaka, Japan) were dissolved in a mixture of chloroform/methanol (1:1) at the ratio of 2:2:1 to one molar concentration. This mixture was dried under a stream of nitrogen for one hour and stored at −40° C. until use. Immediately before use, the dried mixture of lipids was resuspended in TBS such that the GM1 concentration was 2.5 mM, and subjected to 10 cycles of freezing/thawing using liquid nitrogen. This lipid suspension was centrifuged at 13,000 rpm for 15 minutes (MX-160, TOMY, Tokyo, Japan), and the resultant pellet was resuspended in TBS such that the GM1 concentration became the same concentration again. Finally, this suspension was sonicated on ice for 5 minutes, repeated three times, using an ultrasonic disrupter (UD-201, output level: 2, TOMY, Tokyo, Japan) equipped with a microtip (TP-030, TOMY, Tokyo, Japan).

2-3) Preparation of Fibril Aβ (fAβ) as a Core for Fibril Formation

Synthesized $A\beta_{1-40}$ (Bachem AG, Switzerland; Lot. 519599;) was dissolved by brief vortexing in about 500 μM ammonia solution at 4° C., and diluted to 50 μM in the incubation buffer (50 mM phosphate buffer, pH7.5; 100 mM NaCl). After incubation at 37° C. for 24 hours, $1.6 \times 10^4$ g of the mixture was centrifuged at 4° C. for three hours. The resultant pellet was resuspended in ice-cold incubation buffer containing 0.005% $NaN_3$ in an Eppendorf tube, sonicated on ice using ultrasonic disrupter (UD-201, output level: 2, TOMY, Tokyo, Japan) equipped with a microtip (TP-030, TOMY, Tokyo, Japan) and stored at 4° C. until use.

2-4) ThT (thioflavin T) assay

The ThT assay was performed in accordance with a method described in the document (H. Naiki, F. Gejyo, Methods Enzymol. 309, 305 (1999)) using a spectrofluorometer (RF-5300PC; Shimadzu Corporation, Kyoto, Japan). Firstly, the Aβ solution prepared in 2-1) was incubated with liposomes at an Aβ concentration of 50 μM (GM1: Aβ=10:1) or with 10 μg/ml of fAβ prepared in 2-3) in PCR tubes (ELT-0.5, Ryocou) at 37° C. using Dry Thermo Unit Incubator (DTU-1B, TIETECH Co. Ltd., Koshigaya, Japan). Immediately before measurement, 5 μl of incubation mixture was taken from each tube and mixed in 995 μl of 50 mM glycine-NaOH buffer (pH 8.5) that contains 5 μM of ThT. Then, optimal fluorescence of amyloid fibrils (excitation wavelength: 450 nm and emission wavelengths: 490 nm) was measured. FIG. 4 is a graph showing the measurement results. In FIG. 4A, ■ denotes fluorescence when the Aβ solution was incubated with liposomes; and Δ denotes fluorescence when the Aβ solution was incubated with fAβ. It is shown that the fluorescence when the incubation was carried out in the presence of liposomes immediately increased without a lag phase and attained equilibrium hyperbolically.

Note here that no increase in fluorescence was observed at all when incubation was carried out in the absence of liposomes or fAβ (the case shown by (○)). FIG. 4B shows a semilogarithmical plot of the difference: F(8)−F(t) versus incubation time (0-24 hrs). F(t) represents the increase in fluorescence as a function of time when Aβ was incubated with liposomes, and F(8) was experimentally determined. Linear regression and correlation coefficient were calculated (r=0.997). It is found that F(t) is expressed by an equation: F'(t)=B−CF(t), i.e., F (t) follows the primary regression model (see reference document 18). Thus, it was shown that the fibril formation in the presence of liposomes proceeds as the primary regression model.

FIG. 4C shows electron micrographs of the mixture incubated for 24 hours following addition of fAβ (upper micrograph) and the mixture incubated for 96 hours following addition of liposomes (lower micrograph). From these results, it is shown that typical amyloid fibrils are formed in the presence of liposomes. Note here that in FIG. 4C, the bar indicates a length of 100 nm.

The above-mentioned results strongly suggest: firstly, soluble Aβ bound to GM1 on the membrane immediately to form a GM1-Aβ complex (GM1-Aβ). Subsequently, the soluble Aβ bound to GM1-Aβ as a heterologus seed. By the soluble Aβ binding to the end of continuously elongating fibril, the formation of amyloid fibrils proceed.

EXAMPLE 3

Verification of Capability of Inhibiting Amyloid Fibril Formation by Antibody 4396C 3-1) Investigation of Binding Capacity of Antibody 4396C It was investigated whether or not the antibody 4396C prepared in Example 1 specifically recognized Aβ bound to GM1 (GM1-Aβ) in liposomes. Firstly, liposomes containing GM1 prepared in Example 2 or liposomes lacking in GM1 (control) were incubated with the Aβ solution prepared in Example 2. Incubated mixture was stored on ice until loading on a carbon-coated ormvarnickel grid. It was incubated with 1% bovine serum albumin at 12° C. for five minutes, thereby blocking non-specific binding. Then, each grid was treated with the antibody 4396C or an antibody 4G8 (a well-known antibody recognizing Aβ: K. S. Kim, et al., Neurosci. Res. Commun. 2, 121 (1988)) at the final concentration of 20 μg/ml at 12° C. for 45 minutes. Thereafter, the grid was treated with 5 nm of gold-labeled anti-mouse IgG (British BioCell International Ltd.) that was diluted to ¹/₂₀ at 12° C. for 60 minutes. Then, negative staining was carried out with 2% uranium acetate.

FIG. 5A shows an electron micrograph of stained image. The left part shows an electron micrograph of a sample when GM1-containing liposomes (CH (cholesterol), SM (sphingomyelin), and GM1 (GM1 ganglioside)) and an Aβ solution were incubated and then stained with the antibody 4396C; a middle part shows an electron micrograph of a sample when GM1-containing liposomes and an Aβ solution were incubated and then stained with an antibody 4G8; and a right part shows an electron micrograph of a sample when liposomes lacking in GM1 (CH (cholesterol) and SM (sphingomyelin)) and an Aβ solution were incubated and then stained with an antibody 4396C. The results show that GM1-containing liposomes are labeled with the antibody 4396C (see left part), but not with the antibody 4G8 (see middle part). Furthermore, it is shown that the antibody 4396 does not recognize liposomes lacking GM1 (see right part). The bar indicates a length of 50 nm. From the results mentioned above, it was shown that the antibody 4396C specifically recognizes GM1-Aβ formed in liposome. Furthermore, it was shown that the antibody 4G8 that is one of the well-known anti-Aβ antibodies could not recognize GM1-Aβ.

Then, the reactivity between the antibody 4396C and GM1 or soluble Aβ was investigated by Western blotting. The Aβ solution prepared in Example 2 blotted (1 ng) on a nitrocellulose membrane was incubated with the antibody 4396C or the antibody 4G8, and then labeled as mentioned above. Thus, the reactivity between Aβ and the respective antibody was investigated. Similarly, the reactivity of the antibody 4396C with respect to GM1 (Wako Pure Chemical Industries Ltd., Osaka, Japan) was investigated. As control for comparison, incubation was carried out using POD-labeled cholera toxin subunit (CTX) (Sigma) instead of the antibody 4396C. FIG. 5B shows a state of the membrane after incubation, showing that the antibody 4396C was reacted with neither soluble Aβ nor GM1.

Subsequently, the reactivity between the antibody 4396C and the aggregated Aβ was investigated. A section of the cerebral cortex of the brain of a patient with Alzheimer's disease was fixed in 4% formaldehyde and embedded in paraffin, then pre-treated with formic acid. Thereafter, immunolabeling was carried out with the antibody 4396C or the antibody 4G8. As shown in FIG. 5C, when the antibody 4G8 was used, neurotic plaques were strongly immunostained (right half part), but not at all immunostained when the antibody 4396C was used (left half part). Arrows indicate vessels in the serial sections.

The above-mentioned series of results show that an intermediate Aβ, i.e., a transient form from soluble Aβ to aggregated Aβ, was generated by binding of Aβ to GM1 and that unlike other well-known anti-Aβ antibodies, the antibody 4396C specifically recognized, not soluble Aβ and aggregated Aβ, but Aβ bound to GM1, i.e., GM1-Aβ.

EXAMPLE 4

It was investigated whether or not the formation of amyloid fibrils in the presence of GM1-containing liposomes could be inhibited by the antibody 4396C.

An Aβ solution and GM1-containing liposomes prepared in Example 2 and the antibody 4396C were concurrently incubated, and the formation of amyloid fibrils was examined by the ThT assay. As control for comparative, incubation was carried out by using an antibody 4G8 instead of the antibody 4396C. FIG. 6A shows the results. The ratio of antibody 4396C molecules to Aβ molecules is 0.3:50 (Δ), 1.3:50 (○), and 4:50 (□), respectively. Furthermore, the ratio of antibody 4G8molecules to Aβ molecules is 4:50 (◊). ■ denotes a result when the incubation was carried out without adding any antibodies. As shown in FIG. 6A, the antibody 4396C inhibits the increase in fluorescence of ThT in a dose-dependent manner. On the contrary, the antibody 4G8, i.e., a different anti-Aβ antibody, did not inhibit the increase in fluorescence at all.

FIG. 6B shows an immunoelectron micrograph of a mixture of synthetic Aβ1140 and 4G8, which were concurrently incubated for 24 hours following the addition of GM1-containing liposomes. The sample was loaded on a grid and directly labeled with immunogold-labeled anti-mouse IgG following the blocking with bovine serum albumin. The bar indicates a length of 100 nm. From the results, it is apparent that the antibody 4G8 binds to the end of a newly formed amyloid fibril.

EXAMPLE 5

Preparation of Human Chimeric Antibody 5-1) Isolation of Human γ-Chain Constant Region Gene and Human λ-Chain Constant Region Gene The human γ-chain constant region DNA and the human λ-chain constant region DNA were obtained from a human lymphocyte cDNA library as a template of DNA complementary to a part of each DNA.

5-2) Preparation of Chimeric H-Chain Vector and Chimeric L-Chain Vector

Firstly, the human γ-chain constant region DNA and the mouse H-chain variable region DNA obtained in Example 1 were ligated, and incorporated into an expression vector "BCMGS Neo vector" (Hajime Toriyama, Bovine papillomavirus vector, Experimental Medicine (supplementary volume), Genetic Engineering Handbook edited by Masami Muramatsu and Hirohito Okayama, YODOSHA CO., LTD., pp. 297-299 (1991)) to form a chimeric H-chain vector. Similarly, the human γ-chain constant region DNA and the mouse L-chain variable region DNA obtained in Example 1 were ligated, and incorporated into an expression vector "BCMGS Neo vector" to form a chimeric L-chain vector.

5-3) Transfection

Two kinds of vectors (chimeric H-chain vector and chimeric L-chain vector) were concurrently transfected into a CHO (Chinese hamster ovary) cell by the lipofectin method, cultivated at 37° C. for a predetermined time, transplanted into a 96-well plate, and selected in DMEM/10% FCS containing 500 μg/ml of neomycin.

The amount of IgG in the culture medium is measured as follows. Anti-human γ-chain (Medical & Biological Laboratories Co., Ltd.: code 103AG) is diluted with PBS to 10 μg/ml, dispensed into a polystyrene microplate in the amount of 100 μl to each well, and sensitized at 4° C. over night. Then, blocking is carried out by using 5% BSA/5% sucrose/PBS at 4° C. over night. 100 μl of sample is reacted at 37° C. for one hour, followed by washing with PBS/0.05% Tween 20. After washing, 4000× diluted peroxidase labeled anti-human IgG (Medical & Biological Laboratories Co., Ltd.: code 208) is reacted at 37° C. for one hour, followed by washing with PBS/0.05% Tween 20. After washing, 100 μl of enzyme-substrate solution is dispensed and reacted at room temperature for 15 minutes. Then, 100 μl of 2N sulfuric acid is dispensed into each well, and $A_{492}$ is measured. For control, human sera (amount of IgG: 200 ng/ml, 20 ng/ml, 2 ng/ml, and 0.2 ng/ml) are used. Thus, a clone exhibiting the largest amount of expression is selected and the culture supernatant is collected. From the collected culture supernatant, an antibody is purified by using a protein A agarose column.

EXAMPLE 6

Preparation of Human CDR-Grafted Antibody 6-1) Design of Human CDR-Grafted Antibody For the H chain and the L chain, sequences exhibiting high homology to the H chain and the L chain of the antibody 4396C are selected from a well-known database (for example, Fast a database search), respectively. Then, a sequence having FRs of these sequences and CDR of the antibody 4396C is designed.

6-2) Preparation of Human CDR-Grafted Antibody Expression Vector

The H-chain variable region DNA and the L-chain variable region DNA, which were designed in 6-1), can be prepared as follows.

Firstly, as shown in FIG. 7, eight synthetic DNAs were prepared. These synthetic DNAs are prepared such that they cover about 400 bp of variable regions with about 20 bp of each DNA being overlapped with other. 10 pmol/10 μl of these synthetic DNAs are treated at 100° C. for five minutes, followed by quenching. The synthetic DNAs 1 and 2, 3 and 4, 5 and 6, and 7 and 8 are mixed respectively, heated in a heat block at 65° C. for 30 minutes, left it stand for 12 hours and subjected to slow annealing. Then, 1 µl of 20 mM dNTP, 1 µl of Sequenase (Amersham), 10 µl of 5× Sequenase Buffer are added, and sterile water is added to total amount of 50 µl finally. The mixture is incubated at 37° C. for one hour. The DNA fragments (1-2, 3-4, 5-6, and 7-8) are subjected to an electrophoresis with 2% agarose, cleaved out, and dissolved in 30 µl of sterile water. Then, 1 µl of Pfu polymerase, 5 µl of DMSO and 9 µl of 10× Pfu buffer are added to 2 µl each of the cleaved DNA fragments 1-2 and 3-4, 5-6 and 7-8. Then, sterile water is added to total amount of 90 µl, and subjected to 6 cycles of PCR under the conditions: at 94° C. for one minute, 55° C. for one minute and 72° C. for two minutes. Then, 1 µl of 10× buffer and 5 µl each of 20 µM primers (a and b, or c and d) are added respectively, and further subjected to 25 cycles of PCR under the conditions: at 94° C. for one minute, 55° C. for one minute and 72° C. for two minutes. PCR-amplified DNA fragments (1-2-3-4 and 5-6-7-8) are cleaved out, dissolved in 30 µl of sterile water, and subjected to 6 cycles of PCR by using 2 µl of the respective DNAs under the above-mentioned conditions. Then, primers e and f are further added and 25 cycles of PCR are carried out under the above-mentioned conditions. The resultant fragments are cleaved out, cloned into a pT7blueT vector, and the sequence is confirmed.

Subsequently, similar to Example 5, an expression vector, "BCMGS Neo vector," a synthetic H-chain variable region DNA provided with restriction enzyme site by PCR and the human γ-chain DNA are ligated so as to prepare a CDR H-chain vector. Similarly, a CDR L-chain vector into which the synthetic L-chain variable region DNA and the human λ-chain DNA were incorporated is prepared.

6-3) Transfection

The CDR H-chain vector and the CDR L-chain vector are concurrently transfected into a CHO cell by the lipofectin method, cultivated at 37° C. for 12 hours, and replanted into a 96-well plate, and selected in DMEM/10% FCS containing 500 µg/ml of neomycin. Thereafter, a clone exhibiting the largest amount of expression is selected by ELISA. The culture supernatant is collected and an antibody is purified by using a Protein A agarose column.

While an embodiment of the invention has been described using specific terms, such description is for illustrative purposes only, and it is to be understood that changes and variations may be made without departing from the spirit or scope of the following claims.

INDUSTRIAL APPLICABILITY

The present invention provides information (amino acid sequence and DNA sequence) of an antibody which is different from a conventionally known antibody raised against a amyloid β-protein and has an activity of recognizing not a soluble amyloid β-protein but GM1 ganglioside bound amyloid β-protein and inhibiting the formation of amyloid fibrils. It also provides an antibody (including antibody fragment) having such an activity. In particular, based on the information of CDR, a humanized antibody can be produced. These antibodies are effective means for diagnosing, preventing and treating Alzheimer's disease.

What is claimed is:

1. A recombinant antibody or antigen-binding fragment thereof having specificity for GM1 ganglioside-bound amyloid β-protein and which inhibits the formation of amyloid fibrils comprising: a heavy chain variable region; and a light chain variable region, wherein the heavy chain variable region comprises complementarity determining regions (CDRs) described in g), h) and i), and the light chain variable region comprises CDRs described in j), k) and l);
   g) CDR 1 consisting of the amino acid sequence of SEQ ID NO. 1;
   h) CDR 2 consisting of the amino acid sequence of SEQ ID NO. 2;
   i) CDR 3 consisting of the amino acid sequence of SEQ ID NO. 3;
   j) CDR 1 consisting of the amino acid sequence of SEQ ID NO. 4;
   k) CDR 2 consisting of the amino acid sequence of SEQ ID NO. 5; and
   l) CDR 3 consisting of the amino acid sequence of SEQ ID NO. 6.

2. The antibody or antigen-binding fragment thereof according to claim 1, wherein the heavy chain variable region comprises the amino acid sequence of SEQ ID NO: 7.

3. The antibody or antigen-binding fragment thereof according to claim 1, wherein the light chain variable region comprises the amino acid sequence of SEQ ID NO: 8.

4. The antibody or antigen-binding fragment thereof according to claim 1, wherein the heavy chain variable region comprises the amino acid sequence of SEQ ID NO: 7; and the light chain variable region comprises the amino acid sequence of SEQ ID NO: 8.

5. The antibody or antigen-binding fragment thereof according to claim 1, which is a humanized antibody.

6. The antibody or antigen-binding fragment thereof according to claim 1, wherein the antibody is isotype IgG1, IgG2, IgG3 or IgG4.

7. The antibody or antigen-binding fragment thereof according to claim 1, wherein the antigen-binding fragment is Fab, Fab', F(ab')$_2$, scFv or dsFv.

* * * * *